US010285647B2

(12) United States Patent
Razavi et al.

(10) Patent No.: US 10,285,647 B2
(45) Date of Patent: May 14, 2019

(54) METHOD AND SYSTEM TO AUTOMATICALLY ASSIGN MAP POINTS TO ANATOMICAL SEGMENTS AND DETERMINE MECHANICAL ACTIVATION TIME

(71) Applicant: Pacesetter Inc., Sunnyvale, CA (US)

(72) Inventors: Hoda Razavi, San Jose, CA (US); Yelena Nabutovsky, Mt. View, CA (US)

(73) Assignee: Pacesetter Inc., Sunnyvale, CA (US)

( * ) Notice: Subject to any disclaimer, the term of this patent is extended or adjusted under 35 U.S.C. 154(b) by 965 days.

(21) Appl. No.: 14/270,191

(22) Filed: May 5, 2014

(65) Prior Publication Data
US 2015/0317448 A1    Nov. 5, 2015

(51) Int. Cl.
| | | |
|---|---|---|
| A61B 5/00 | (2006.01) |
| A61B 6/00 | (2006.01) |
| A61B 5/027 | (2006.01) |
| A61B 5/055 | (2006.01) |
| A61B 5/02 | (2006.01) |
| G06F 19/00 | (2018.01) |
| A61B 5/042 | (2006.01) |
| A61B 5/0432 | (2006.01) |
| A61B 5/04 | (2006.01) |
| A61B 5/0265 | (2006.01) |
| A61B 5/11 | (2006.01) |
| A61B 6/12 | (2006.01) |
| G16H 50/50 | (2018.01) |
| A61B 5/029 | (2006.01) |

(52) U.S. Cl.
CPC ............ *A61B 5/6852* (2013.01); *A61B 5/027* (2013.01); *A61B 5/02028* (2013.01); *A61B 5/0265* (2013.01); *A61B 5/042* (2013.01); *A61B 5/04012* (2013.01); *A61B 5/0432* (2013.01); *A61B 5/1102* (2013.01); *A61B 5/7221* (2013.01); *A61B 5/7485* (2013.01); *A61B 6/12* (2013.01); *A61B 6/503* (2013.01); *G06F 19/00* (2013.01); *G06F 19/321* (2013.01); *G16H 50/50* (2018.01); *A61B 5/02007* (2013.01); *A61B 5/029* (2013.01); *A61B 5/055* (2013.01); *A61B 5/11* (2013.01); *A61B 5/1107* (2013.01); *A61B 6/4441* (2013.01); *A61B 6/487* (2013.01); *A61B 2576/023* (2013.01)

(58) Field of Classification Search
None
See application file for complete search history.

(56) References Cited

U.S. PATENT DOCUMENTS

| | | |
|---|---|---|
| 5,391,199 A | 2/1995 | Ben-Haim |
| 5,713,367 A | 2/1998 | Arnold et al. |
| 6,233,476 B1 | 5/2001 | Strommer et al. |
| 6,301,496 B1 | 10/2001 | Reisfeld |
| 6,609,027 B2 | 8/2003 | Kroll et al. |
| 6,633,686 B1 | 10/2003 | Bakircioglu et al. |
| 6,728,562 B1 | 4/2004 | Budd et al. |
| 6,751,492 B2 | 6/2004 | Ben-Haim |
| 6,978,168 B2 | 12/2005 | Beatty et al. |
| 7,197,354 B2 | 3/2007 | Sobe |
| 7,263,297 B2 | 8/2007 | Hauck et al. |
| 7,276,064 B2 | 10/2007 | Paul et al. |
| 7,338,486 B2 | 3/2008 | Sliwa et al. |
| 7,386,339 B2 | 6/2008 | Strommer et al. |
| 7,505,809 B2 | 3/2009 | Strommer et al. |
| 7,697,973 B2 | 4/2010 | Strommer et al. |
| 7,881,769 B2 | 2/2011 | Sobe |
| 8,016,764 B1 | 9/2011 | Shelchuk |
| 8,195,292 B2 | 6/2012 | Noren et al. |
| 8,849,381 B2 | 9/2014 | Mason et al. |
| 9,162,067 B1 | 10/2015 | Farazi et al. |
| 2003/0093067 A1 | 5/2003 | Panescu |

(Continued)

FOREIGN PATENT DOCUMENTS

| | | |
|---|---|---|
| EP | 1 070 480 A2 | 1/2001 |
| EP | 1 508 300 A1 | 2/2005 |

(Continued)

OTHER PUBLICATIONS

Non-Final Office Action dated Dec. 11, 2015; Related U.S. Appl. No. 14/703,460.

Non-Final Office Action dated Sep. 30, 2015; Related U.S. Appl. No. 14/270,181.

Notice of Allowance dated Dec. 8, 2015; Related U.S. Appl. No. 12/347,216.

USPTO, "Final Office Action for U.S. Appl. No. 14/703,749", dated Jan. 23, 2017.

USPTO, "Non-Final Office Action for U.S. Appl. No. 14/703,735", dated Jan. 12, 2017.

(Continued)

*Primary Examiner* — Lori A. Clow

(74) *Attorney, Agent, or Firm* — Theresa A. Raymer

(57) ABSTRACT

A method and system are provided for assigning map points to anatomical segments of a heart. The method and system utilize an intravascular mapping tool configured to be inserted into at least one of the endocardial or epicardial space. The mapping tool is maneuvered to select locations proximate to surfaces of the heart, while collecting map points at the select locations to form a ROI data set. The method and system store the ROI data set in a data storage and defines apical, basal and circumferential landmarks within the ROI data set. The method and system automatically calculate circumferential and longitudinal segment boundaries, associated with wall segments of the heart, based on the apical, basal and circumferential landmarks. The method and system automatically assign segment identifiers (IDs) to the map points based on locations of the map points relative to the circumferential and longitudinal boundaries, the segment IDs associated with wall segments of the heart.

24 Claims, 14 Drawing Sheets

(56) References Cited

U.S. PATENT DOCUMENTS

| | | |
|---|---|---|
| 2003/0233039 A1 | 12/2003 | Shao et al. |
| 2005/0154282 A1 | 7/2005 | Li et al. |
| 2006/0245536 A1 | 11/2006 | Boing |
| 2007/0055142 A1 | 3/2007 | Webler et al. |
| 2007/0073179 A1 | 3/2007 | Afonso et al. |
| 2007/0100332 A1 | 5/2007 | Paul et al. |
| 2007/0106146 A1 | 5/2007 | Altmann et al. |
| 2007/0181139 A1 | 8/2007 | Hauck |
| 2007/0244479 A1 | 10/2007 | Beatty et al. |
| 2007/0270705 A1 | 11/2007 | Starks |
| 2007/0299352 A1 | 12/2007 | Harlev |
| 2008/0009758 A1 | 1/2008 | Voth |
| 2008/0091193 A1 | 4/2008 | Kauphusman et al. |
| 2008/0190438 A1 | 8/2008 | Harlev |
| 2009/0163904 A1 | 6/2009 | Miller et al. |
| 2009/0171345 A1 | 7/2009 | Miller et al. |
| 2009/0306732 A1* | 12/2009 | Rosenberg ........... A61B 5/0422 607/9 |
| 2010/0168550 A1 | 7/2010 | Byrd et al. |
| 2010/0265059 A1 | 10/2010 | Ryu |
| 2011/0190593 A1 | 8/2011 | McNair et al. |
| 2011/0208038 A1 | 8/2011 | Konofagou et al. |
| 2011/0243401 A1 | 10/2011 | Zabair et al. |
| 2012/0184863 A1 | 7/2012 | Harlev et al. |
| 2013/0222415 A1 | 8/2013 | Vilsmeier |
| 2013/0272592 A1 | 10/2013 | Eichler et al. |
| 2015/0045867 A1 | 2/2015 | Krishnan et al. |
| 2015/0133802 A1 | 5/2015 | Nabutovsky et al. |
| 2015/0141765 A1 | 5/2015 | Razavi et al. |
| 2015/0141858 A1 | 5/2015 | Razavi et al. |
| 2017/0042481 A1 | 2/2017 | Olson |

FOREIGN PATENT DOCUMENTS

| | | |
|---|---|---|
| EP | 2 757 528 A1 | 7/2014 |
| WO | 97/24981 A2 | 7/1997 |
| WO | 2012/090148 A1 | 7/2012 |

OTHER PUBLICATIONS

USPTO, "Non-Final Office Action for U.S. Appl. No. 14/703,744", dated Jan. 13, 2017.
USPTO, "Non-Final Office Action for U.S. Appl. No. 14/270,186", dated Feb. 27, 2017.
USPTO, "Non-Final Office Action for U.S. Appl. No. 14/478,707", dated Mar. 2, 2017.
Final Office Action dated Jan. 22, 2016; Related U.S. Appl. No. 14/270,176.
Non-Final Office Action dated Feb. 8, 2016; Related U.S. Appl. No. 14/270,181.
Notice of Allowance dated Feb. 25, 2016; Related U.S. Appl. No. 14/328,513.
Notice of Allowance dated Feb. 25, 2016; Related U.S. Appl. No. 14/703,760.
Non-Final Office Action dated Mar. 28, 2016; Related U.S. Appl. No. 14/703,749.
Notice of Allowance dated Apr. 19, 2016; Related U.S. Appl. No. 14/270,181.
Notice of Allowance dated Jun. 22, 2015; Related U.S. Appl. No. 14/328,523.
Bogatyrenko, Evgeniya et al., Efficient Physics-Based Tracking of Heart Surface Motion for Beating Heart Surgery Robotic Systems, International Journal of Computer Assisted Radiology and Surgery, vol. 6, No. 3, pp. 387-399, Aug. 2010.
International Search Report and Written Opinion in PCT Application No. PCT/US2015/028206 (dated Jul. 22, 2015).
Quatember, Bernhard et al., "Geometric Modeling and Motion Analysis of the Epicardial Surface of the Heart", Mathematics and Computers in Simulation, vol. 81, No. 3, pp. 608-622, Nov. 2010.
Segars, W. Paul et al., "A Realistic Spline-Based Dynamic Heart Phantom", IEEE Transactions on Nuclear Science, vol. 46, No. 3, pp. 503-506, Jun. 1999.
U.S. Appl. No. 09/107,731, filed Jun. 30, 1998 for "Chamber Mapping System".
Advisory Action dated Aug. 10, 2015; Related U.S. Appl. No. 12/347,216.
Amendment filed Jun. 25, 2015; Related U.S. Appl. No. 12/347,216.
Final Office Action dated May 4, 2015; Related U.S. Appl. No. 12/347,216.
Amendment filed Dec. 18, 2014; Related U.S. Appl. No. 12/347,216.
Non-Final Office Action dated Oct. 2, 2014; Related U.S. Appl. No. 12/347,216.
Advisory Action dated May 1, 2014; Related U.S. Appl. No. 12/347,216.
Amendment filed Apr. 24, 2014; Related U.S. Appl. No. 12/347,216.
Applicant Interview Summary, dated Apr. 21, 2014; Related U.S. Appl. No. 12/347,216.
Final Office Action dated Feb. 25, 2014; Related U.S. Appl. No. 12/347,216.
Amendment filed Feb. 4, 2014; Related U.S. Appl. No. 12/347,216.
Non-Final Office Action dated Nov. 21, 2013; Related U.S. Appl. No. 12/347,216.
Amendment filed Oct. 29, 2012; Related U.S. Appl. No. 12/347,216.
Advisory Action dated Oct. 11, 2012; Related U.S. Appl. No. 12/347,216.
Amendment filed Oct. 1, 2012; Related U.S. Appl. No. 12/347,216.
Advisory Action dated Sep. 12, 2012; Related U.S. Appl. No. 12/347,216.
Amendment filed Aug. 28, 2012; Related U.S. Appl. No. 12/347,216.
Final Office Action dated Jun. 29, 2012; Related U.S. Appl. No. 12/347,216.
Amendment filed May 14, 2012; Related U.S. Appl. No. 12/347,216.
Interview Summary, dated Feb. 28, 2012; Related U.S. Appl. No. 12/347,216.
Non-Final Office Action dated Feb. 13, 2012; Related U.S. Appl. No. 12/347,216.
Notice of Allowance dated Oct. 27, 2015; Related U.S. Appl. No. 14/328,523.
USPTO, "Non-Final Office Action for U.S. Appl. No. 14/703,757", dated Apr. 6, 2017.
USPTO, "Notice of Allowance for U.S. Appl. No. 14/270,176", dated May 20, 2016.
Notice of Allowance dated Apr. 18, 20017, Related U.S. Appl. No. 14/703,749.
Notice of Allowance dated Jun. 2, 20017; Related U.S. Appl. No. 14/703,744.
St. Jude Medical, "EnSite Velocity Cardiac Mapping System, Model EE3300, v.4," Feb. 28, 2013, 238 pages.
Office Action dated Jul. 5, 2017; Related U.S. Appl. No. 14/270,191.
Notice of Allowance dated May 9, 20017; Related U.S. Appl. No. 14/703,749.

* cited by examiner

METHOD AND SYSTEM TO AUTOMATICALLY ASSIGN MAP POINTS TO ANATOMICAL SEGMENTS AND DETERMINE MECHANICAL ACTIVATION TIME

RELATED APPLICATION DATA

The present application is related to the following applications: U.S. provisional application Ser. No. 61/906,311, filed Nov. 19, 2013, titled "METHOD AND SYSTEM TO ASSESS MECHANICAL DYSSYNCHRONY BASED ON MOTION DATA COLLECTED BY A NAVIGATION SYSTEM", U.S. provisional application Ser. No. 61/910,630, filed Nov. 19, 2013, titled "METHOD TO MEASURE CARDIAC MOTION USING A CARDIOVASCULAR NAVIGATION SYSTEM", U.S. provisional application Ser. No. 61/906,305, filed Nov. 19, 2013, titled "METHOD AND SYSTEM TO ASSESS MECHANICAL DYSSYNCHRONY BASED ON MOTION DATA COLLECTED BY A NAVIGATION SYSTEM", U.S. patent application Ser. No. 14/270,181, filed May 5, 2014, titled "METHOD AND SYSTEM TO CHARACTERIZE MOTION DATA BASED ON NEIGHBORING MAP POINTS", U.S. patent application Ser. No. 14/270,186, filed. May 5, 2014, titled "METHOD AND SYSTEM FOR CALCULATING STRAIN FROM CHARACTERIZATION DATA OF A CARDIAC CHAMBER", and U.S. patent application Ser. No. 14/270,176, filed May 5, 2014, titled "METHOD AND SYSTEM FOR DISPLAYING A THREE DIMENSIONAL VISUALIZATION OF CARDIAC MOTION", all of which are expressly incorporated herein by reference in their entirety.

BACKGROUND OF THE INVENTION

Embodiments of the present disclosure generally relate to methods and systems for automatically assigning map points to anatomical segments. Embodiments of the present disclosure relate to methods and systems for determining mechanical activation times for map points of the heart.

A prevailing theory regarding response to cardiac resynchronization therapy (CRT) is that the therapy corrects mechanical dyssynchrony of the heart. Therefore, methods and systems have been proposed to accurately assess the dyssynchrony. The dyssynchrony information can be used to predict response to CRT as well as optimize LV lead placement and CRT programming parameters. Today, most methods to assess dyssynchrony involve echocardiography. However, in certain circumstances, conventional echocardiography techniques may experience errors that lead to inaccurate characterization of dyssynchrony. Further, questions still remain as to which specific approach(es) are preferred for assessing dyssynchrony, with various indices being used with mixed success. Further still, echocardiography studies are not intraoperative, therefore do not capture certain information that is otherwise of interest during the CRT procedure.

Today, various cardiovascular navigation systems exist. For example, the St. Jude Medical MediGuide™ (MDG) cardiovascular navigation system is a 3-D electromagnetic navigation system that provides real-time position and orientation information regarding sensors embedded in electrophysiologic tools. The MDG system is integrated with a fluoroscopic (or other diagnostic) imaging system and tracks the sensors continuously within an imaging volume defined by the fluoroscopic system, on both live and recorded background diagnostic images.

Recently, it has been proposed to utilize the MDG system to identify a desired (e.g., optimal) location for placement of a left ventricular (LV) lead. For example, the MDG system systematically records information associated with various endocardial and epicardial locations in the LV. Depending on the size of the heart and other factors during the procedure, there may be various numbers endocardial LV map points and various numbers of epi-cardial map points at which the MDG system obtains recordings for each patient.

A need exists for improved methods and systems that can automatically assign map points, collected by cardiovascular navigation systems, to anatomical segments. A need also exists for improved methods and systems that can determine mechanical activation times associated with the map points.

SUMMARY

In accordance with embodiments herein, a method is provided for assigning map points to anatomical segments of a heart, the method comprises utilizing an intravascular mapping tool configured to be inserted into at least one of the endocardial or epicardial space. The mapping tool is maneuvered to select locations proximate to surfaces of the heart, while collecting map points at the select locations to form a ROI data set. The method stores the ROI data set in a data storage and defines apical, basal and circumferential landmarks within the ROI data set. The method automatically calculates circumferential and longitudinal segment boundaries, associated with wall segments of the heart, based on the apical, basal and circumferential landmarks. The method automatically assigns segment identifiers (IDs) to the map points based on locations of the map points relative to the circumferential and longitudinal boundaries, the segment IDs associated with wall segments of the heart Optionally, the defining operation comprises performing a computer implemented analysis of the ROI data set to: i) identify an apical end region and radial regions of the ROI data set; ii) identify an apical data outlier that is located proximate to the apical end region; iii) identify a lateral data outlier that is located proximate to at least one of the radial regions; and iv) designate the apical and basal landmarks based on the apical and radial data outliers. Optionally, the defining operation comprises performing a computer implemented analysis of the ROI data set to: i) designate apical and basal landmarks relative to a longitudinal axis extending through the ROI data set; ii) identify a circumferential data outlier that is located laterally, relative to the longitudinal axis, at an outer extent of the ROI data set; and iii) designate a circumferential landmark based on the circumferential data outliers.

Optionally, the method comprises collecting at least one of electrophysiology, hemodynamic and motion mapping data associated with each of the map points. The method may collect the map points until an extent of the ROI data set exceeds a predetermined threshold in at least one of a longitudinal direction and a radial direction relative to a reference axis. The defining operation may include manually maneuvering the mapping tool to select points proximate to the surface of the heart; and receiving a user input designating the select points as the apical, basal and circumferential landmarks. The user input designated points may be proximate to the tricuspid valve, the septal wall and a proximal portion of a coronary sinus branch as the select points. The method may comprise utilizing the select points to define a basal plane extending through a base of the left ventricle; and projecting a long axis from the apical landmark orthogonally to the basal plane.

In accordance with embodiments, a system is provided for assigning map points to anatomical segments of a heart. The system comprises a data storage configured to store map points collected by an intravascular mapping tool configured to be inserted into at least one of the endocardial or epicardial space, the mapping tool maneuvered to select locations proximate to surfaces of the heart, while collecting the map points at the select locations to form a ROI data set. The system further comprises a landmark module configured to define apical, basal and circumferential landmarks within the ROI data set. A processor in the system is configured to: i) automatically calculate circumferential and longitudinal segment boundaries relative to the heart, for the ROI data set, based on the apical, basal and circumferential landmarks; and ii) automatically assign segment identifiers (IDs) to the map points based on locations of the map points relative to the circumferential and longitudinal boundaries, the segment IDs associated with wall segments of the heart.

Optionally, the landmark module may include a processor and instructions directing the processor to perform a computer implemented analysis of the ROI data set to: identify an apical end region and radial regions of the ROI data set; identify an apical data outlier that is located proximate to the apical end region; identify a lateral data outlier that is located proximate to at least one of the radial regions; and designating the apical and basal landmarks based on the apical and radial data outliers.

In accordance with embodiments herein, methods and systems are provided that identify the time of mechanical activation at each motion map point from one or more main directional motion components. The methods and systems identify the time of mechanical activation by first finding at least two of the radial, longitudinal, and circumferential motion components, then choosing one or more of these components for use to find the time of mechanical activation. The selection between radial, longitudinal and circumferential motion components is based on various characteristics or criteria. For example, the component selection may be based on one or more of i) timing of each of the motion components to determine which motion component to use; ii) location of the map point relative to the heart to determine which motion component to use and/or iii) quality of the shape of the motion waveform exhibited in each direction component to determine which motion component to use.

In accordance with embodiments herein, a method is provided for determining mechanical activation times (MATs) associated with map points of a heart. The method comprises obtaining a region of interest (ROI) data set comprising a plurality of point specific (PS) motion data representative of motion at select map points, the PS motion data for at least a portion of the map points comprising motion components indicative of motion along at least corresponding first and second directions. The method comprises analyzing a component preference characteristic (CPC) to designate at least one of the motion components; and determining a MAT for a current map point based on the at least one motion component of the PS motion data designated by the CPC in the analyzing operation.

Optionally, the CPC represents a time characteristic that is to be identified from the PS motion data, the time characteristic representing one of an onset and an end for one of a contraction action and an extension action of a region of interest. The determining operation may determine the MAT based on an earlier occurrence of contraction onset exhibited in radial and longitudinal component motion waveforms. The determining operation may determine the MAT based on a later occurrence of a contraction end event exhibited in radial and longitudinal component motion waveforms. Optionally, the motion components include at least two of radial, circumferential and longitudinal component motion waveforms, the determining operation determines the MAT based on an event of interest from at least one of radial, circumferential and longitudinal component motion waveforms.

In accordance with embodiments, the CPC may represent a location characteristic indicating a wall segment in which the map point is located, the location characteristic representing one of apical, middle, basal, anteroseptal, anterior, lateral, septal, inferior, and posterior wall segments, the determining operation using at least one of the motion components associated with the wall segment indicated by the CPC. The analyzing operation may include identifying whether a current map point is in a wall segment for which motion is predominately in the radial direction or predominately in the longitudinal direction; wherein the determining operation uses a longitudinal component motion waveform associated with the current map point to identify the MAT, when the motion is predominately in the longitudinal direction, and the determining operation uses the radial component motion waveform associated with the current map point to identify the MAT, when the motion is predominately in the radial direction.

Optionally, the CPC may represent a quality characteristic indicating clarity of a characteristic of interest in motion waveforms associated with the motion components. Optionally, the analyzing operation may comprise analyzing one or more characteristics of interest of motion waveforms for the motion components, the characteristics of interest including at least one of angle of a select waveform segment, a presence of notches in a vicinity of onset and/or end systole, a number of peaks/valleys, or a number of changes in slope in the motion waveforms.

In accordance with embodiments, the method further comprises assigning a clarity score to each of the motion waveform motion components, the CPC based on the clarity scores, the clarity scores indicating a distinctiveness of a characteristic of interest in the motion waveforms.

In accordance with embodiments a system is provided for determining mechanical activation times (MATs) associated with map points of a heart. The system comprises a data storage configured to store an ROI data set comprising a plurality of point specific (PS) motion data representative of motion at select map points proximate to the heart, the PS motion data for at least a portion of the map points comprising motion components indicative of motion along at least corresponding first and second directions. The system further comprises a processor configured to: i) analyze a component preference characteristic (CPC) to designate at least one of the motion components; and ii) determine a MAT for a current map point based on the at least one motion component of the PS motion data designated by the CPC in the analyzing operation.

Optionally, the CPC represents a time characteristic that is to be identified from the PS motion data, the time characteristic representing one of an onset and an end for one of a contraction action and an extension action of a region of interest. Optionally, the processor is configured to determine the MAT based on an earlier occurrence of a contraction onset exhibited in radial and longitudinal component motion waveforms. The processor may determine the MAT based on a later occurrence of a contraction end event exhibited in radial and longitudinal motion waveforms. The processor may be configured to: identify whether a current map point is in a wall segment for which motion is predominately in the radial direction or predominately in the longitudinal direction; use a longitudinal component motion waveform associated with the current map point to identify the MAT, when the motion is predominately in the longitudinal direction, and use the radial component motion waveform associated with the current map point to identify the MAT, when the motion is predominately in the radial direction.

DETAILED DESCRIPTION

Figure 1:
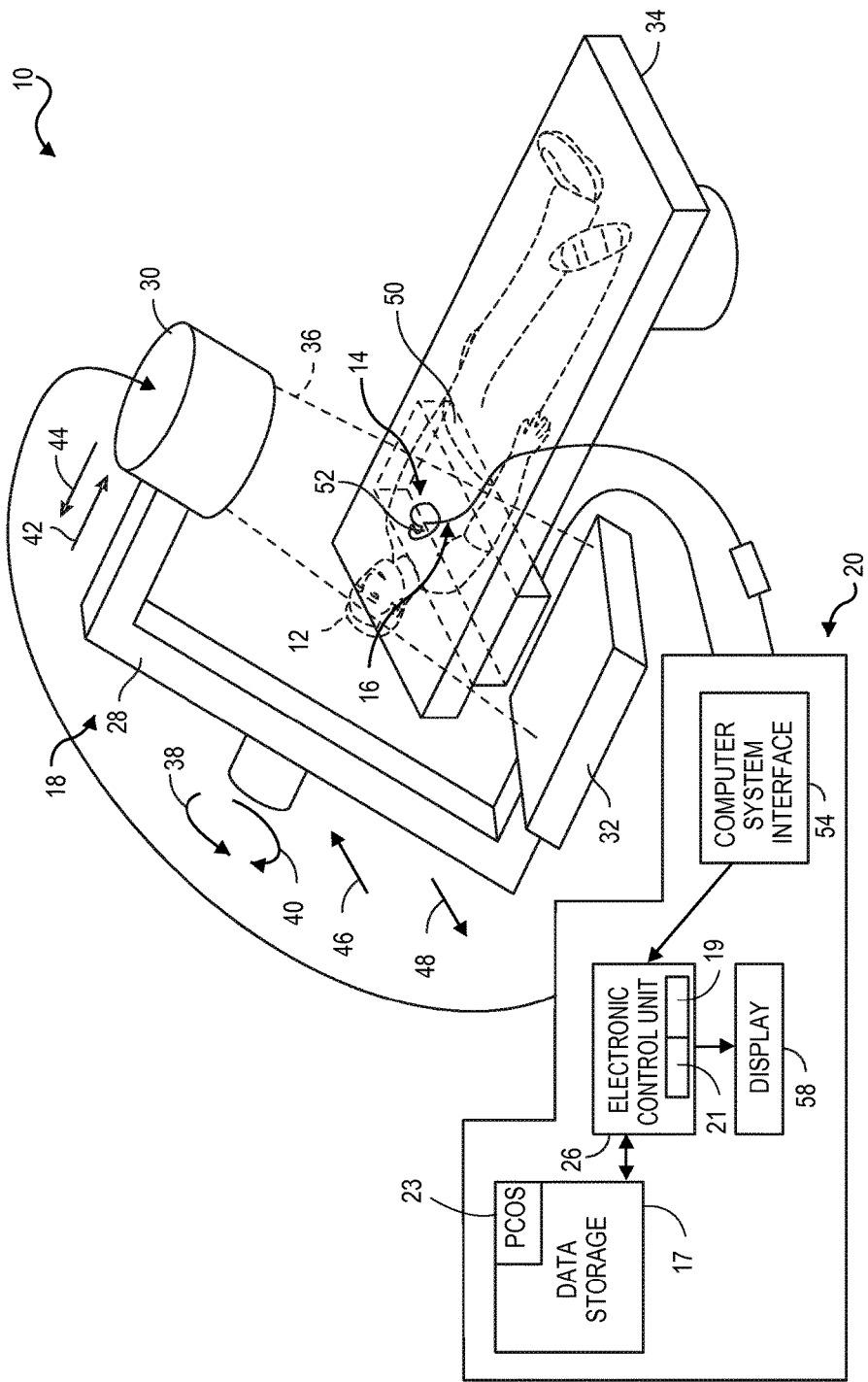
FIG. 1 illustrates an imaging and navigation system for use in imaging an anatomical region of the heart and to collect motion data in connection with embodiments.

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

The methods herein may be implemented as a software algorithm, package, or system that directs one or more hardware circuits or circuitry to perform the actions described herein. For example, the operations of the methods herein may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

Embodiments herein may be implemented with, and/or utilize aspects of, the methods and system described in the following co-pending applications: U.S. provisional application Ser. No. 61/906,311, filed Nov. 19, 2013, titled "METHOD AND SYSTEM TO ASSESS MECHANICAL DYSSYNCHRONY BASED ON MOTION DATA COLLECTED BY A NAVIGATION SYSTEM", U.S. provisional application Ser. No. 61/910,630, filed Nov. 19, 2013, titled "METHOD TO MEASURE CARDIAC MOTION USING A CARDIOVASCULAR NAVIGATION SYSTEM", U.S. provisional application Ser. No. 61/906,305, filed Nov. 19, 2013, titled "METHOD AND SYSTEM TO ASSESS MECHANICAL DYSSYNCHRONY BASED ON MOTION DATA COLLECTED BY A NAVIGATION SYSTEM", U.S. patent application Ser. No. 14/270,181, filed May 5, 2014, titled "METHOD AND SYSTEM TO CHARACTERIZE MOTION DATA BASED ON NEIGHBORING MAP POINTS" U.S. patent application Ser. No. 14/270,186, filed May 5, 2014, titled "METHOD AND SYSTEM FOR CALCULATING STRAIN FROM CHARACTERIZATION DATA OF A CARDIAC CHAMBER", U.S. patent application Ser. No. 14/270,176, filed May 5, 2014, titled "METHOD AND SYSTEM FOR DISPLAYING A THREE DIMENSIONAL VISUALIZATION OF CARDIAC MOTION", which is filed on or about the same day as the present application, all of which are expressly incorporated herein by reference in their entirety.

FIG. 1 illustrates an imaging and navigation system 10 for use in imaging an anatomical region of a patient 12 such as a heart 14. Optionally, the imaging equipment may be removed entirely. A medical tool 16 is implanted within the anatomical region, such as for example, an electrophysiological (EP) mapping catheter or a catheter generally described or shown in U.S. Pat. No. 7,881,769, the entire disclosure of which is incorporated herein by reference. The medical tool 16 includes a plurality of electrophysiological sensors 52 that may be placed on the endocardial or epicardial surface of the left ventricle of the heart 14. The electrophysiological sensors 52 may be attached to the distal or proximal end of the medical tool 16, or any point in between. The electrophysiological sensors 52 measure a position and an electrical potential or an electric current of biological cells and tissues, and are transmitted to an electronic control unit (ECU) 26. For example, the electrophysiological sensors 52 may be positioned by the medical tool 16 to measure the electrical potential along a portion of the wall of the heart 14. It should be understood, however, that the electrophysiological sensors 52 could be used in a variety of anatomical regions within the heart 14 or other organs in which motion characterization may be of interest.

System 10 may include an imaging system 18 and a medical device navigation system 20. The system 10 may also include a registration system for registering a group of images of the anatomical region of patient 12 in a navigation coordinate system of the navigation system 20 as generally described and shown in U.S. Patent Publication 2013/0272592 and International Pub. No. WO 2012090148, the entire disclosures of which are incorporated herein by reference.

The imaging system 18 is provided to acquire images of heart 14 or another anatomical region of interest and comprises a fluoroscopic imaging system in the illustrated embodiment. Although a fluoroscopic imaging system is described in this embodiment, the embodiments described herein may find use with other types of imaging systems, for example, but without limitation, computed tomography (CT) imaging systems and three-dimensional radial angiography (3DRA) systems. System 18 may include a C-arm support structure 28, a radiation emitter 30, and a radiation detector 32. Emitter 30 and detector 32 are disposed on opposite ends of support structure 22 and disposed on opposite sides of patient 12 as patient 12 lays on an operation table 34. Emitter 30 and detector 32 define a field of view 36 and are positioned such that the field of view 36 includes the anatomical region of interest as patient 12 lays on operation table 34. Imaging system 18 is configured to capture images of anatomical features and other objects within field of view 36. Support structure 28 may have freedom to rotate about the patient as shown by lines 38, 40. Support structure 28 may also have freedom to slide along lines 42, 44 (i.e. along the cranio-caudal axis of patient 12) and/or along lines 46, 48 (i.e. perpendicular to the cranio-caudal axis of patient 12). Rotational and translational movement of support structure 28 yields corresponding rotational and translational movement of field of view 36.

Imaging system 18 may acquire a group of images of an anatomical region of patient 12 by first shifting along lines 42, 44, 46, 48 to place the anatomical region of interest within the field of view 36. Second, support structure 28 may rotate radiation emitter 30 and radiation detector 32 about patient 12, keeping the anatomical region within field of view 36. Imaging system 18 may capture images of the anatomical region as support structure 28 rotates, providing a group of two-dimensional images of the anatomical region from a variety of angles. The group of images may be communicated to ECU 26 for image processing and display. The group of images may comprise a sequence of images taken over a predetermined time period.

Navigation system 20 is provided to determine the position of medical tool 16 within the body of patient 12 and to permit a clinician to navigate tool 16 within the body. In the illustrated embodiment, system 20 comprises a magnetic navigation system in which magnetic fields are generated in the anatomical region and position sensors associated with tool 16 generate an output that changes responsive to the position of the sensors within the magnetic field. System 20 may comprise, for example, the systems generally shown and described in, for example, U.S. Pat. Nos. 6,233,476, 7,197,354, 7,386,339, and 7,505,809 all of which are incorporated by reference in their entirety. Although a magnetic navigation system is shown in the illustrated embodiment, it should be understood that the invention could find use with a variety of navigation systems including those based on the creation and detection of axes specific electric fields. Navigation system 20 may include a transmitter assembly 50.

The transmitter assembly 50 is conventional in the art and may include a plurality of coils arranged orthogonally to one another to produce a magnetic field in and/or around the anatomical region of interest. It should be noted that, although transmitter assembly 50 is shown under the body of patient 12 and under table 34, transmitter assembly 50 may be placed in another location, such as attached to radiation emitter 30, from which the magnetic field generators can project a magnetic field in the anatomical region of interest. In accordance with embodiments, the transmitter assembly 50 is within the field of view 36. The ECU 26 may control the generation of magnetic fields by transmitter assembly 50.

The electrophysiological sensors 52 are configured to generate an output dependent on the relative position of electrophysiological sensors 52 within the field generated by transmitter assembly 50. In FIG. 1, the electrophysiological sensor 52 and medical tool 16 are shown disposed around the heart 14. As medical tool 16 is guided to and through the region of interest, the navigation system 20 determines the location of the electrophysiological sensors 52 in the generated field, and thus the position of medical tool 16 as well. The tool 16 may be guided to endocardial locations and/or epicardial locations, to collect point specific (PS) motion data. The navigation system 20 further determines a navigation coordinate of the navigation coordinate system. The navigation system 20 and medical tool 16 are used to create a "point cloud" as the medical tool 16 is moved around the heart. The navigation system 20, in general, records every position that the medical tool 16 visits. Thus, when the user moves the medical tool 16 in a sphere, eventually a point cloud would be created that is in the shape of a filled in sphere. The navigation system also collects motion data for a subset of the points at which the medical tool 16 is positioned. The motion data is collected for map points that represent a small subset of the point cloud. For example, the motion data may be collected when the medical tool 16 pauses at a desired location and collects data at the same location for several cardiac cycles. The motion data collected over the several cardiac cycles at all of the desired locations collectively is referred to as the ROI data set. The point cloud may be used to designate the landmarks for segmentation, such as to find the apex, base, and LVOT. The motion data for the map points are used, as explained herein, for assigning points to segments and for finding time of mechanical activation.

A data storage 17 is configured to store map point data collected by the intravascular mapping tool 16 that is configured to be inserted into at least one of the endocardial or epicardial space. The mapping tool 16 is maneuvered to select locations proximate to surfaces of the heart, while collecting the data for map points at the select locations to form a ROI data set 23. A landmark module 19 is configured to define apical, basal and circumferential landmarks within the ROI data set. A processor 21 in the module 19 is configured to: automatically calculate circumferential and longitudinal segment boundaries relative to the heart, for the ROI data set 23, based on the apical, basal and circumferential landmarks; and automatically assign segment identifiers (IDs) to the map points based on locations of the map points relative to the circumferential and longitudinal boundaries, the segment IDs associated with wall segments of the heart.

The landmark module 19 includes instructions directing the processor 21 to perform a computer implemented analysis of the ROI data set 23 to: identify an apical end region and radial regions of the ROI data set; identify an apical data outlier that is located proximate to the apical end region; identify a lateral data outlier that is located proximate to at least one of the radial regions; and designating the apical and basal landmarks based on the apical and radial data outliers.

The landmark module 19 includes instructions directing the processor 21 to perform a computer implemented analysis of the ROI data set 23 to: designate apical and basal landmarks relative to a longitudinal axis extending through the ROI data set; identify a circumferential data outlier that is located laterally, relative to the longitudinal axis, at an outer extent of the ROI data set; and designate a circumferential landmark based on the circumferential data outliers.

The map point data stored by the data storage 17 comprises point specific map point data representative of at least one of electrophysiology, hemodynamic and motion mapping data associated with each of the map points.

Optionally, the landmark module 19 includes instructions directing the processor 21 to perform a computer implemented analysis of the ROI data set 23 automatically when an extent of the ROI data set exceeds a predetermined threshold in at least one of a longitudinal direction and a radial direction relative to a reference axis.

Optionally, the landmark module 19 may be coupled to a user interface to receive inputs from a user while the user manually maneuvers the mapping tool 16 to select points proximate to the surface of the heart. The user interface receives a user input designating the select points as the apical, basal and circumferential landmarks. The user input designates points proximate to the tricuspid valve, the septal wall and a proximal portion of a coronary sinus branch as the select points. Instructions direct the processor 21 to: utilize the select points to define a basal plane extending through a base of the left ventricle; and project a long axis from the apical landmark to the basal plane. Optionally, the processor 21 may be configured to utilize the apical, basal and circumferential landmarks to define a cylindrical coordinate system; and converting coordinates for the map points from a Cartesian coordinate system to the cylindrical coordinate system. Optionally, the processor 21 may be configured to define the circumferential landmark to correspond to the left ventricular outflow track (LVOT). Optionally, the processor 21 may be configured to utilize the LVOT as a reference point to define the circumferential boundaries to separate anteroseptal, anterior, lateral, septal, inferior, and posterior wall segments.

The system 20 may also determine mechanical activation times (MATs) associated with map points of a heart. The data storage 17 stores an ROI data set 23 comprising a plurality of point specific (PS) motion data representative of motion at select map points proximate to the heart. The PS motion data for at least a portion of the map points comprising motion components indicative of motion along at least corresponding first and second directions. The processor 21 analyzes a component preference characteristic (CPC) to designate at least one of the motion components, and determines a MAT for a current map point based on the at least one motion component of the PS motion data designated by the CPC in the analyzing operation.

The CPC may represent a time characteristic that is to be identified from the PS motion data. The time characteristic represents one of an onset and an end for one of a contraction action and an extension action of a region of interest. Optionally, the processor 21 may determine the MAT based on an earlier occurrence of a contraction onset exhibited in radial and longitudinal component motion waveforms. Optionally, the processor 21 may determine the MAT based on a later occurrence of a contraction end event exhibited in radial and longitudinal component motion waveforms.

Optionally, the motion components include at least two of radial, circumferential and longitudinal component motion waveforms, the determining operation determines the MAT based on an event of interest from at least one of radial, circumferential and longitudinal component motion waveforms.

Optionally, the CPC represents a location characteristic indicating a wall segment in which the map point is located, the location characteristic representing one of apical, middle, basal, anteroseptal, anterior, lateral, septal, inferior, and posterior wall segments. The processor 21 may be configured to use at least one of the motion components associated with the wall segment indicated by the CPC.

The processor 21 may identify whether a current map point is in a wall segment for which motion is predominately in the radial direction or predominately in the longitudinal direction, use a longitudinal component motion waveform associated with the current map point to identify the MAT, when the motion is predominately in the longitudinal direction, and use a radial component motion waveform associated with the current map point to identify the MAT, when the motion is predominately in the radial direction.

Optionally, the CPC represents a quality characteristic indicating a clarity of a characteristic of interest in motion waveforms associated with the motion components. The processor 21 may analyze one or more characteristics of interest of motion waveforms for the motion components. The characteristics of interest include at least one of angle of a select waveform segment, a presence of notches in a vicinity of onset and/or end systole, a number of peaks/valleys, or a number of changes in slope in motion waveforms. The processor 21 may be configured to assign a clarity score to each of the motion components, the CPC based on the clarity scores, the clarity scores indicating a distinctiveness of a characteristic of interest in the motion components.

Additionally or alternatively, the motion waveform of the PS motion data at a select map point may represent a waveform indicative of strain (e.g., tissue deformation) or strain rate at the select map point from a beginning to an end of a cardiac cycle. Strain is a measure of tissue deformation, and is defined as the change in length normalized to the original length. There may be three primary directions of strain in the heart: a longitudinal direction (e.g., traversing along an axis formed by longitudinal divisions), a radial direction, and/or a circumferential direction (e.g., traversing along an axis formed by circumferential divisions). Strain rate is the rate at which the tissue deformation or strain occurs. Strain rate may be measured as the difference in velocity between two map points (e.g., toward each other, away from each other) along the heart wall normalized to the distance between the two map points.

For example, the ECU 26 may set a position reference point at the beginning of the cardiac cycle. During the cardiac cycle, the ECU 26 may compare instantaneous positions of the tool 16 at the map point, over the cardiac cycle, against the positions of surrounding map points to acquire the PS motion data representing strain of the map point. The PS motion data may define the strain over the cardiac cycle. Optionally, the ECU 26 may determine the strain rate of the map point by calculating the derivative or change in the strain over time. The strain or strain rate at a select map point may be relative to one or more other map points. Optionally, the select map point may have multiple strains or strain rates associated there with.

One or more patient reference sensors (not shown) are on the body of the patient 12, for example, on the chest. The patient reference sensors measure a displacement and orientation of the patient reference sensors relative to a predetermined reference point, such as, the electrophysiological sensors 52 or the transmitter assembly 50.

The ECU 26 of the navigation system 20 may include or represent hardware circuits or circuitry that include and/or are connected with one or more logic based devices, such as processors, microprocessors, controllers, microcontrollers, or other logic based devices (and/or associated hardware, circuitry, and/or software stored on a tangible and non-transitory computer readable medium or memory). The ECU 26 may receive a plurality of input signals including signals generated by medical tool 16, imaging system 18, the electrophysiological sensors 52, an operator system interface 54, and the patient reference sensors and generate a plurality of output signals including those used to control tool 16, imaging system 18, the display 58. ECU 26 may also receive an input signal from an organ monitor (not shown), such as an ECG monitor, and sort or segregate images from imaging system 18 based on a timing signal of a monitored organ. For example, ECU 26 may sort images based on the phase of the patient's cardiac cycle at which each image was collected, as more fully described in U.S. Pat. No. 7,697,973, which is hereby incorporated by reference in its entirety.

Figure 2A:
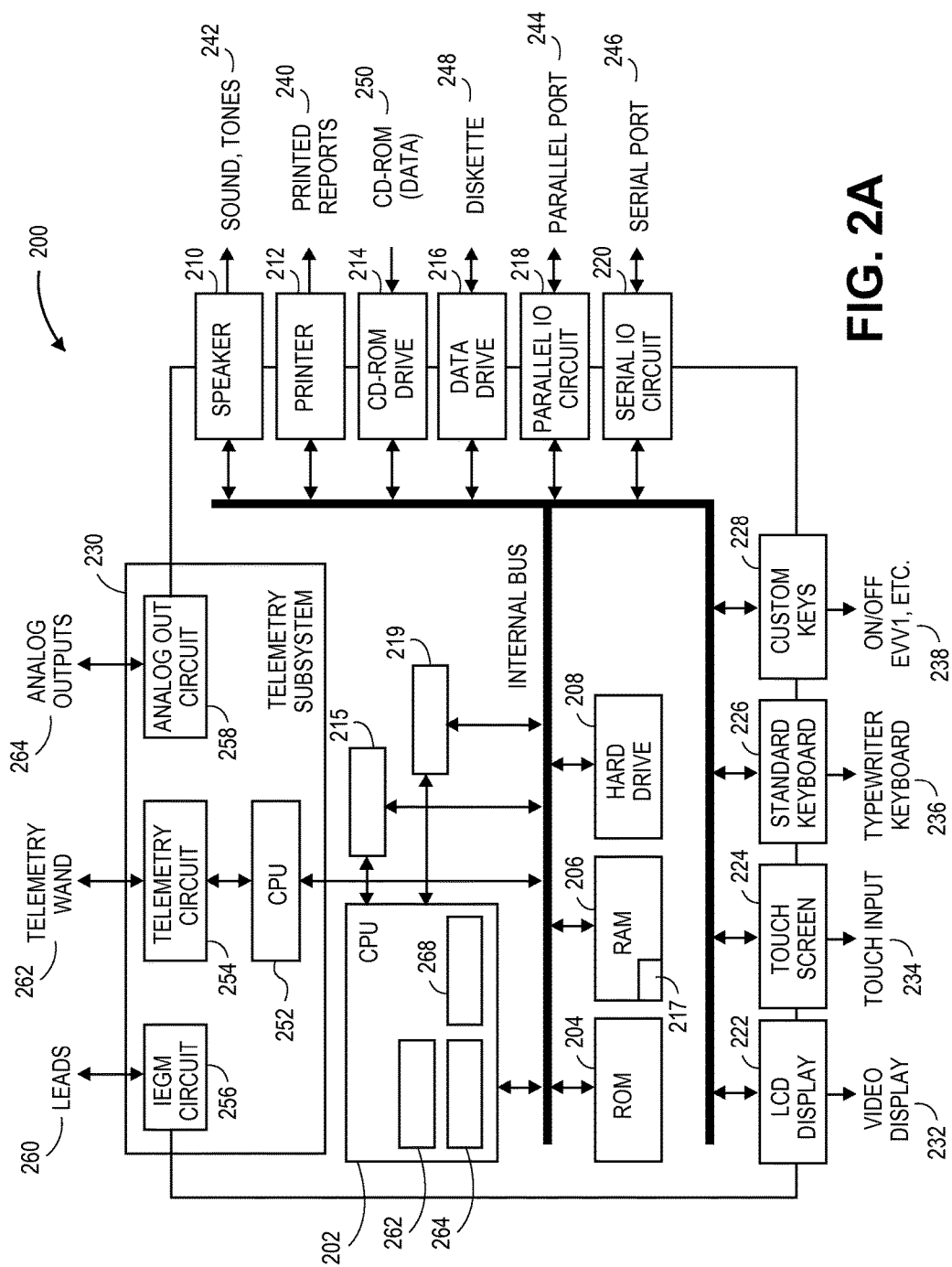
FIG. 2A illustrates a system for analyzing motion data in accordance with embodiments.

FIG. 2A illustrates a functional block diagram of an external system 200 that is operated in accordance with the processes described herein to collect, store and analyze point specific motion data and to interface with users and with implantable medical devices. The system 200 may be a workstation, a portable computer, an IMD programmer, a PDA, a cell phone and the like. The system 200 includes an internal bus that connects/interfaces with a Central Processing Unit (CPU) 202, ROM 204, RAM 206, a hard drive 208, the speaker 210, a printer 212, a CD-ROM drive 214, a floppy drive 216, a parallel I/O circuit 218, a serial I/O circuit 220, the display 222, a touch screen 224, a standard keyboard connection 226, custom keys 228, and a telemetry subsystem 230. The internal bus is an address/data bus that transfers information between the various components described herein. The hard drive 208 may store operational programs as well as data, such as waveform templates and detection thresholds.

The CPU 202 typically includes a microprocessor, a microcontroller, or equivalent control circuitry, designed specifically to control interfacing with the external device 200, the navigation system 20, an implantable device and the like. The CPU 202 may include RAM or ROM memory, logic and timing circuitry, state machine circuitry, and I/O circuitry to interface with the IMD 100. The display 222 (e.g., may be connected to the video display 232). The touch screen 224 may display graphic information relating to the IMD 100. The display 222 displays various information related to the processes described herein. The touch screen 224 accepts a user's touch input 234 when selections are made. The keyboard 226 (e.g., a typewriter keyboard 236) allows the user to enter data to the displayed fields, as well as interface with the telemetry subsystem 230. Furthermore, custom keys 228 turn on/off 238 (e.g., EVVI) the system 200. The printer 212 prints copies of reports 240 for a physician to review or to be placed in a patient file, and speaker 210 provides an audible warning (e.g., sounds and tones 242) to the user. The parallel I/O circuit 218 interfaces with a parallel port 244. The serial I/O circuit 220 interfaces with a serial port 246. The floppy drive 216 accepts diskettes 248. Optionally, the floppy drive 216 may include a USB port or other interface capable of communicating with a USB device such as a memory stick. The CD-ROM drive 214 accepts CD ROMs 250.

The CPU 202 is configured to analyze motion data collected by the cardiovascular navigation system to determine a level of mechanical dyssynchrony exhibited by a heart. The CPU 202 receives access to ROI data sets, collected as explained herein. The CPU 202 includes a point specific motion data (PSMD) collection analysis circuit module 262 that divides the motion data into sectors associated with corresponding phases of the cardiac cycle. The CPU 202 includes an analysis circuit module (ACM) 264 that analyzes the sectors of the motion data to determine at least one of a magnitude and a direction of motion at the corresponding map point of the wall of the heart during the associated phases of the cardiac cycle. The analysis circuit module 264 assesses at least one of the magnitude and direction of motion occurring at the corresponding map points of the wall. The ACM 264 may use all of the motion data associated with a map point, or only analyze one or more motion components, such as the radial or longitudinal motion component. The analysis circuit module 264 performs the assessment for at least a portion of the phases of the cardiac cycle.

The system 200 may also be configured to assign map points to anatomical segments of a heart. One or more of the ROM 204, RAM 206 and hard drive 208 may individually or collectively represent a data storage configured to store data (e.g., motion data, electrophysiology data, hemodynamic data) associated with map points collected by an intravascular mapping tool (e.g., 16 or otherwise). As explained herein, the mapping tool 16 is maneuvered to select locations proximate to surfaces of the heart, while collecting the map point data at the select locations to form a ROI data set.

Figure 2B:
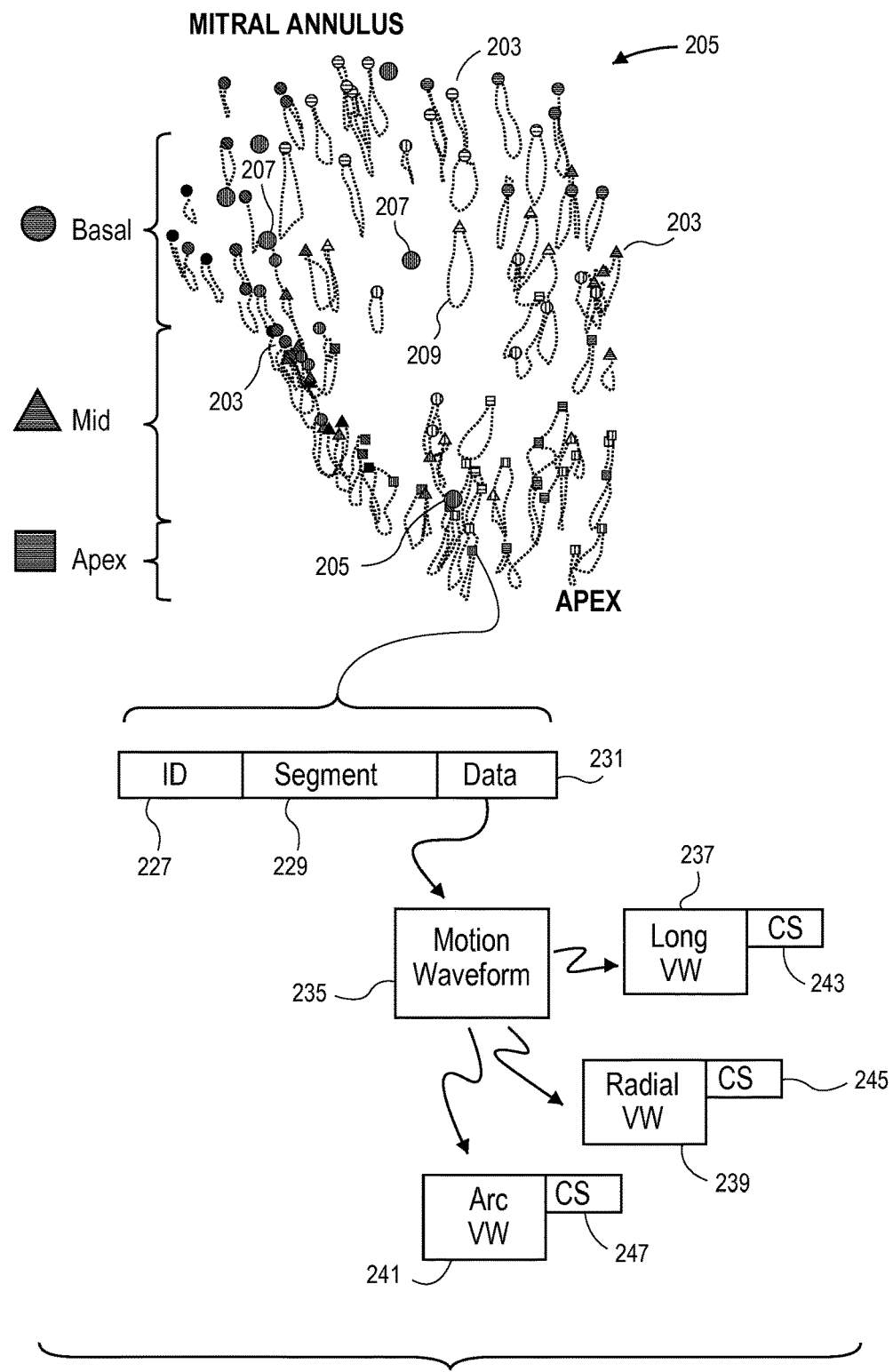
FIG. 2B illustrates a graphical representation of a set of endocardial map points for which motion data is collected in accordance with embodiments.

FIG. 2B illustrates a graphical representation 205 of a set of endocardial map points for which motion data is collected. The circles, triangles and squares illustrate a location of each associated map point 203, at a select point in time in the cardiac cycle. When collecting motion data for each map point 203, the map points 203 move over a closed path throughout the cardiac cycle. The closed path over which each map point moves represents a trajectory 209. In FIG. 2B, the respective trajectories 209 are shown in dashed lines for each map point 203. Anatomical markers 207 and 205 at the mitral annulus and the apex, respectively, are shown.

The system 200 stores (in a data storage) data, coordinates, segmentation and other information, collectively referred to as map point data 223, in connection with each map point 203. The map point data 223 includes a map point identifier (MPID) 227 for the map point 203, a wall segment 229 to which the map point 203 is assigned (e.g., in connection with the processes of FIGS. 3-8). The map point data 223 also include point specific motion data 231. The PS motion data 231 may be recorded in various manners. By way of example only, and without being limiting, the PS motion data 231 may include a map point starting location denoted in one or both of a base coordinate system such as the Cartesian coordinate system and/or a transition coordinate system such as the cylindrical coordinate system. The PS motion data 231 may further include a starting point in time at which the starting location was collected. The PS motion data 231 may further include a series of incremental position changes along each of the axes of the coordinate system. For example, when utilizing a Cartesian or cylindrical coordinate system, the incremental position changes may represent incremental changes along X, Y, and Z axes, or along longitudinal, radial and circumferential axes. Each incremental change in location is either a predetermined incremental time after the start time, or an incremental time stamp is recorded with each incremental change in location in the PS motion data.

In FIG. 2B, the PS motion data 231 may be characterized as a composite waveform 235 along a resultant composite component, or alternatively/additionally, as individual motion components along corresponding directions/axes. For example, the PS motion data 231 may be divided into a longitudinal component waveform 237, a radial component waveform 239, and a circumferential component waveform 241. As explained below in connection with the processes of FIGS. 9-14, one or more of the component waveforms 237, 239 and 241 may be individually assessed for motion information, such as to determine dyssynchrony and the like. The complete set of the PS motion data 231 for all of the map points 203 represents the ROI data set, such as denoted at 219 in the RAM 206. The map points shown in FIG. 2B form at least a portion of a ROI data set as the ROI data set includes the motion data associated with each map point over one or more cardiac cycles. One or more ROI data sets 219 are stored in a data storage (e.g., RAM, ROM, hard drive, etc.).

The system 200 includes a landmark circuit module (LCM) 219 configured to define apical, basal and circumferential landmarks within the ROI data set 217. The LCM 219 may be configured to automatically calculate circumferential and longitudinal segment boundaries relative to the heart, for the ROI data set, based on the apical, basal and circumferential landmarks. The LCM 219 may be configured to automatically assign segment identifiers (IDs) 229 to the map points 203 based on locations of the map points 203 relative to the circumferential and longitudinal boundaries. The segment IDs 219 are associated with wall segments of the heart. The LCM 219 includes a processor and instructions directing the processor to perform a computer implemented analysis of the ROI data set to: identify an apical end region and radial regions of the ROI data set; identify an apical data outlier that is located proximate to the apical end region; identify a lateral data outlier that is located proximate to at least one of the radial regions; and designating the apical and basal landmarks based on the apical and radial data outliers. The LCM 219 may also perform a computer implemented analysis of the ROI data set 217 to: designate apical and basal landmarks relative to a longitudinal axis extending through the ROI data set; identify a circumferential data outlier that is located laterally, relative to the longitudinal axis, at an outer extent of the ROI data set; and designate a circumferential landmark based on the circumferential data outliers. The LCM 219 may perform a computer implemented analysis of the ROI data set 217 automatically when an extent of the ROI data set exceeds a predetermined threshold in at least one of a longitudinal direction and a radial direction relative to a reference axis.

The map points that are stored by the data storage comprises point specific map point data representative of at least one of electrophysiology, hemodynamic and motion mapping data associated with each of the map points.

The LCM 219 is coupled to a user interface (e.g., the keyboard 226, touch screen 224, custom keys 228 and display 222) to receive inputs from a user while the user manually maneuvers the mapping tool to select points proximate to the surface of the heart. The user interface receiving a user input designating the select points as the apical, basal and circumferential landmarks. The user input designates points proximate to the tricuspid valve, the septal wall and a proximal portion of a coronary sinus branch as the select points. The LCM 219 further comprising instructions directing the processor to: utilize the select points to define a basal plane extending through a base of the left ventricle; and project a long axis from the apical landmark to the basal plane.

The system 200 includes a coordinate conversion circuit module (CCCM) 215 that is configured to utilize the apical, basal and circumferential landmarks to define a cylindrical coordinate system, and converting coordinates for the map point data from a Cartesian coordinate system to the cylindrical coordinate system. Optionally the CCCM 215 may convert map point data between other coordinate systems. By way of example, as part of the coordinate conversion process, the CCCM 215 is configured to define the circumferential landmark to correspond to the left ventricular outflow track (LVOT). The CCCM 215 utilizes the LVOT as a reference point to define the circumferential boundaries to separate anteroseptal, anterior, lateral, septal, inferior, and posterior wall segments.

In accordance with embodiments, the system 200 may be used for determining mechanical activation times (MATs) associated with map points of a heart. The system 200 includes instructions (e.g., stored in ROM 204 or cash on the CPU 202) to instruct the CPU 202 to analyze a component preference characteristic (CPC) to designate at least one of the motion components; and determine a MAT for a current map point based on the at least one motion component of the PS motion data designated by the CPC in the analyzing operation. The CPC represents a time characteristic that is to be identified from the PS motion data. The time characteristic may represent one of an onset and an end for one of a contraction action and an extension action of a region of interest. The CPU 202 may be configured to determine the MAT based on an earlier occurrence of a contraction onset exhibited in radial and longitudinal component motion waveforms. The CPU 202 may be configured to determine the MAT based on a later occurrence of a contraction end event exhibited in radial and longitudinal component motion waveforms.

By way of example, the motion components may include at least two of radial, circumferential and longitudinal component motion waveforms 239, 241, and 243. The CPU 202 determines the MAT based on an event of interest from at least one of radial, circumferential and longitudinal component motion waveforms 239, 241 and 243. The CPC represents a location characteristic indicating a wall segment in which the map point is located, the location characteristic representing one of apical, middle, basal, anteroseptal, anterior, lateral, septal, inferior, and posterior wall segments.

The CPU 202 is configured to use at least one of the motion components associated with the wall segment indicated by the CPC.

Optionally, the CPU 202 may be configured to: identify whether a current map point is in a wall segment for which motion is predominately in the radial direction or predominately in the longitudinal direction; use a longitudinal component motion waveform associated with the current map point to identify the MAT, when the motion is predominately in the longitudinal direction, and use a radial component motion waveform associated with the current map point to identify the MAT, when the motion is predominately in the radial direction. The CPC represents a quality characteristic indicating a clarity of a characteristic of interest in motion waveforms associated with the motion components. The CPU 202 analyzes one or more characteristics of interest of motion waveforms for the motion components. The characteristics of interest includes at least one of angle of a select waveform segment, a presence of notches in a vicinity of onset and/or end systole, a number of peaks/valleys, or a number of changes in slope in motion waveforms. The CPU 202 is configured to assign a clarity score to each of the motion components, the CPC based on the clarity scores, the clarity scores indicating a distinctiveness of a characteristic of interest in the motion components.

The endocardial map points have been segmented automatically, in accordance with embodiments herein, in the longitudinal direction. The map points classified in the basal segment are shown as circles, while map points classified in the mid-ventricular segment are shown as triangles, and map points classified in the apical segment are shown as squares.

A dyssynchrony measure circuit module 268 calculates a measure of mechanical dyssynchrony associated with the map points of the wall based on at least one of i) whether the map points move in a select direction during select phases of the cardiac cycle and/or ii) whether the map points move by a select amount during the select phases.

As one example, the measure circuit module 268 may determine, as the measure of dyssynchrony, a proportion of the map points (out of a global set of map points, out of all map points in a corresponding segment and the like) that are moving in the select direction. For example, the select direction may represent at least one of inward during a systole phase and outward during a diastole phase. As another example, the measure circuit module 268 may calculate, as the measure, a percentage of a number of map points that move in the select direction out of a total (global or within a common segment) number of map points.

The display 222 displays a dyssynchrony score based on the measure of dyssynchrony in connection with at least one of lead placement for a cardiac resynchronization therapy (CRT) device or programming optimization for a CRT device. The dyssynchrony score may be presented as a numeric value, a color according to a color coded score range, a graph, a word (e.g., high, medium, low) and the like.

The telemetry subsystem 230 includes a central processing unit (CPU) 252 in electrical communication with a telemetry circuit 254, which communicates with both an IEGM circuit 256 and an analog out circuit 258. The circuit 256 may be connected to leads 260. The circuit 256 is also connected to the implantable leads 114, 116 and 118 to receive and process IEGM cardiac signals as discussed above. Optionally, the IEGM cardiac signals sensed by the leads 114, 116 and 118 may be collected by the IMD 100 and then transmitted, to the system 200, wirelessly to the telemetry subsystem 230 input.

The telemetry circuit 254 is connected to a telemetry wand 262. The analog out circuit 258 includes communication circuits to communicate with analog outputs 264. The system 200 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the system 200 to the IMD 100.

Figure 3:
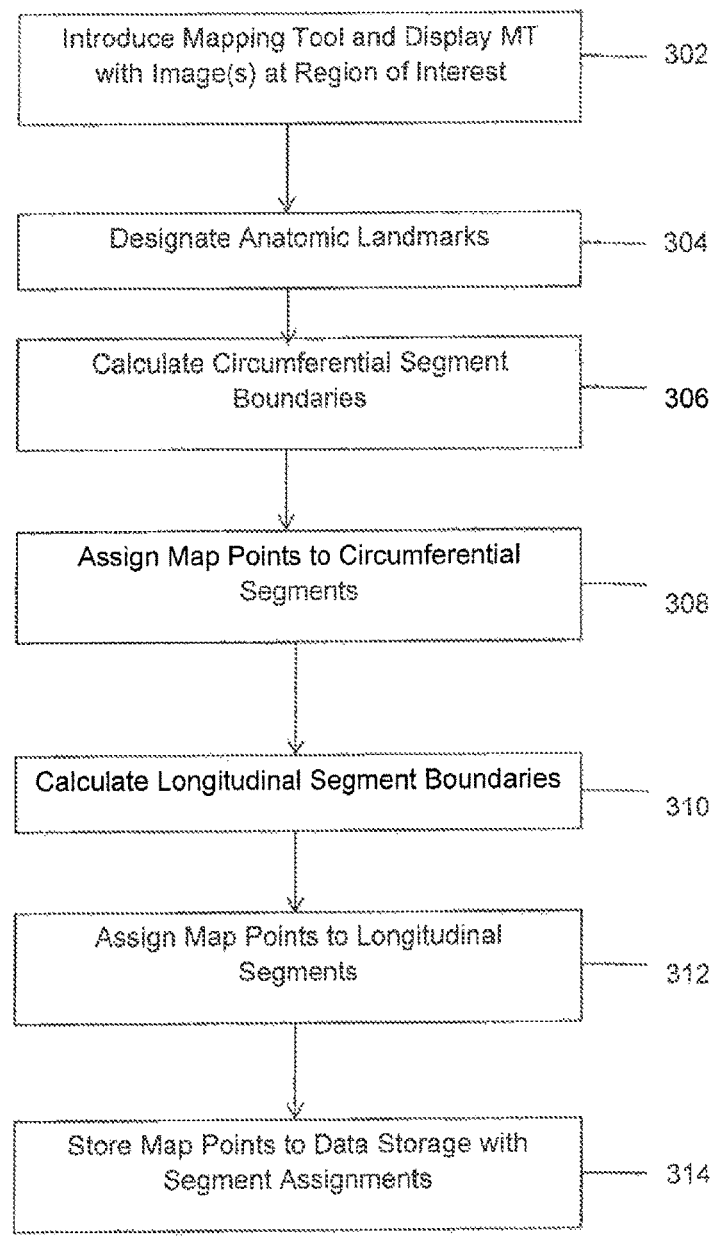
FIG. 3 illustrates a method performed in accordance with embodiments for assigning map points to anatomical segments of the heart.

FIG. 3 illustrates a method performed in accordance with embodiments herein for assigning map points to anatomical segments of the heart. Throughout the present application, examples are provided in connection with mapping the left ventricle (LV). It should be recognized that the operations described herein may be used to map other regions of the heart. When mapping other regions of interest in the heart, different reference points and landmarks may be used.

Beginning at 302, a mapping tool is introduced into the patient proximate to a region of interest. Images are displayed to the user. The images may be collected from various diagnostic imaging modalities (e.g. fluoroscopy, X-ray, MR, ultrasound, CT, PET, SPECT and the like). Information from the guidance system, regarding the mapping tool, is combined with the images of the region of interest, and graphical representations are displayed of the mapping tool, in combination with the diagnostic image(s). For example, the mapping tool may be displayed superimposed upon the diagnostic image(s). By way of example, the physician may utilize an intravascular mapping tool that is configured to be inserted proximate to the heart, endocardially and/or epicardially. The physician maneuvers the mapping tool between multiple locations of interest that are proximate to select areas on interior and/or exterior surfaces of the heart. For example, the physician may manipulate a mapping tool within the right atrium and/or right ventricle to collect endocardial mapping data associated with interior surfaces of the chambers of the heart. Additionally or alternatively, the physician may maneuver the mapping tool along one or more veins that extend about an exterior of a select region/chamber of the heart, such as the left atrium and/or left ventricle, to collect epicardial mapping data.

In the examples discussed herein, the mapping system is configured to map motion information regarding map points distributed across various surfaces of the heart. Alternatively or in addition, the mapping system may represent an electrophysiology monitoring system that collects electrical activity at various select locations within out outside the heart. Alternatively or in addition, the mapping system may represent a hemodynamic monitoring system that collects hemodynamic data at various select locations within the heart and/or cardiovascular network.

While the physician (or other user) maneuvers the mapping tool between select locations, map point data is collected at each select location, such as point specific motion data, electrophysiology data, hemodynamic data and the like. During an intravascular procedure, the map point data is continuously or periodically collected and added to data collection, generally referred to as an ROI data set. The ROI data set expands over time thereby increasing an amount of information regarding the electrical and/or mechanical behavior of the region of interest within the heart. The ROI data set is stored in a data storage, such as at a local terminal or workstation, a local area network, a wide area network, on a network, or at a remote data storage facility.

As explained herein, various analyses may be performed iteratively upon the ROI data set throughout the data collection process. It is not necessary for a complete ROI data set to be collected before performing the analysis described hereafter.

At 304, the method designates anatomic landmarks by defining apical, basal and circumferential landmarks within the ROI data set. As explained herein, the anatomical landmarks may be designated through manual operations or automatic calculations based on analysis of the ROI data set. The landmarks are located at various locations based upon the shape and nature of the region of interest. For example, at least one landmark is located proximate to, or at, the apex of the region of interest. Another landmark is located at or proximate to a middle of a base of the region of interest, while another landmark is located circumferentially from the base at an outer limit of the region of interest. For example, when the region of interest represents the right or left ventricle, the apex landmark represents the apex of the RV or LV. The basal landmark represents the base of the RV or LV and the circumferential landmark represents the left or right ventricular outflow tract.

One or more axes may be defined from the landmarks. For example, a long axis of the RV or LV is defined as a line connecting the apex to the basal point/landmark. A circumferential line is drawn from the basal landmark to the circumferential landmark. The long axis and circumferential line are used to position and orient a transformation coordinate system. For example, the long axis may be used as a Z-axis and the circumferential line is used as the circumferential line of the cylindrical coordinate system. The long axis and circumferential line are used as a basis to convert the point data from a base coordinate system, such as the Cartesian coordinate system, to a coordinate system associated with the regions of interest. For example, location coordinates for point data may be converted from XYZ Cartesian coordinates to longitudinal, radial and circumferential coordinates of the cylindrical coordinates.

At 306, the method automatically calculates circumferential segment boundaries, within the ROI data set, based on the apical, basal and circumferential landmarks.

At 308, the method assigns map points to the circumferential segments as defined at 306. In order to automatically assign each map point, the method determines a corresponding segment of the anatomical map. To do so, in at least one embodiment, the method defines a reference line between the basal landmark and circumferential landmark. The circumferential location of each map point ($\theta_m$) at a predefined point in the cardiac cycle, such as at the peak of the QRS complex, is compared against the circumferential landmark ($\theta_{LVOT}$). Each map point is assigned to the corresponding wall segment, where the circumferential landmark is used to identify a reference wall segment, such as the anteroseptal wall segment. Segment boundaries of the first wall segment are defined as ($\theta_{LVOT}-\pi/6-$tolerance)<$\theta_m\le(\theta_{LVOT}+\pi/6+$tolerance) with the option of including a circumferential tolerance on the order of $\pi/36$. The definitions of the other wall segments include the subsequent addition or subtraction of multiples of ($\pi/3+$tolerance) until the entire circumference of a region of interest (e.g., LV) is assigned to the appropriate wall segment.

At 310, the method calculates the longitudinal segment boundaries. At 312, the method assigns map points to the longitudinal segments based on the longitudinal segment boundaries. For example, the method performs segmentation along the long axis for definition of apical vs. mid-ventricular vs. basal points. The longest available length of the long axis ($L_{Long\ Axis}$) is determined. An apical portion (AP) parameter is then defined which determines the extent of the apical segments and $L_{Long\ Axis}$ is divided by AP, such that any point with a longitudinal coordinate less than L/AP is assigned to the apex. A typical value for AP may be 3, in which the apical segments cover ⅓ of the length of the entire wall from apex to base. Next, the remaining points with longitudinal coordinates less than $$\frac{L_{LongAxis}(AP+1)}{2AP}$$

are assigned to the mid-ventricular segments and those with longitudinal coordinates more than this value are assigned to the basal segments. A longitudinal tolerance can also be introduced to allow for some flexibility in this assignment.

In accordance with 306 to 312, the method automatically calculates circumferential and longitudinal segment boundaries, for the ROI data set, based on the apical, basal and circumferential landmarks. The method then automatically assigns segment identifiers to the map points, where the segment identifiers are associated with segments of the heart that are separated by the circumferential and longitudinal boundaries. At 314, the map points are stored in a data storage with associated segment assignments.

Figure 4:
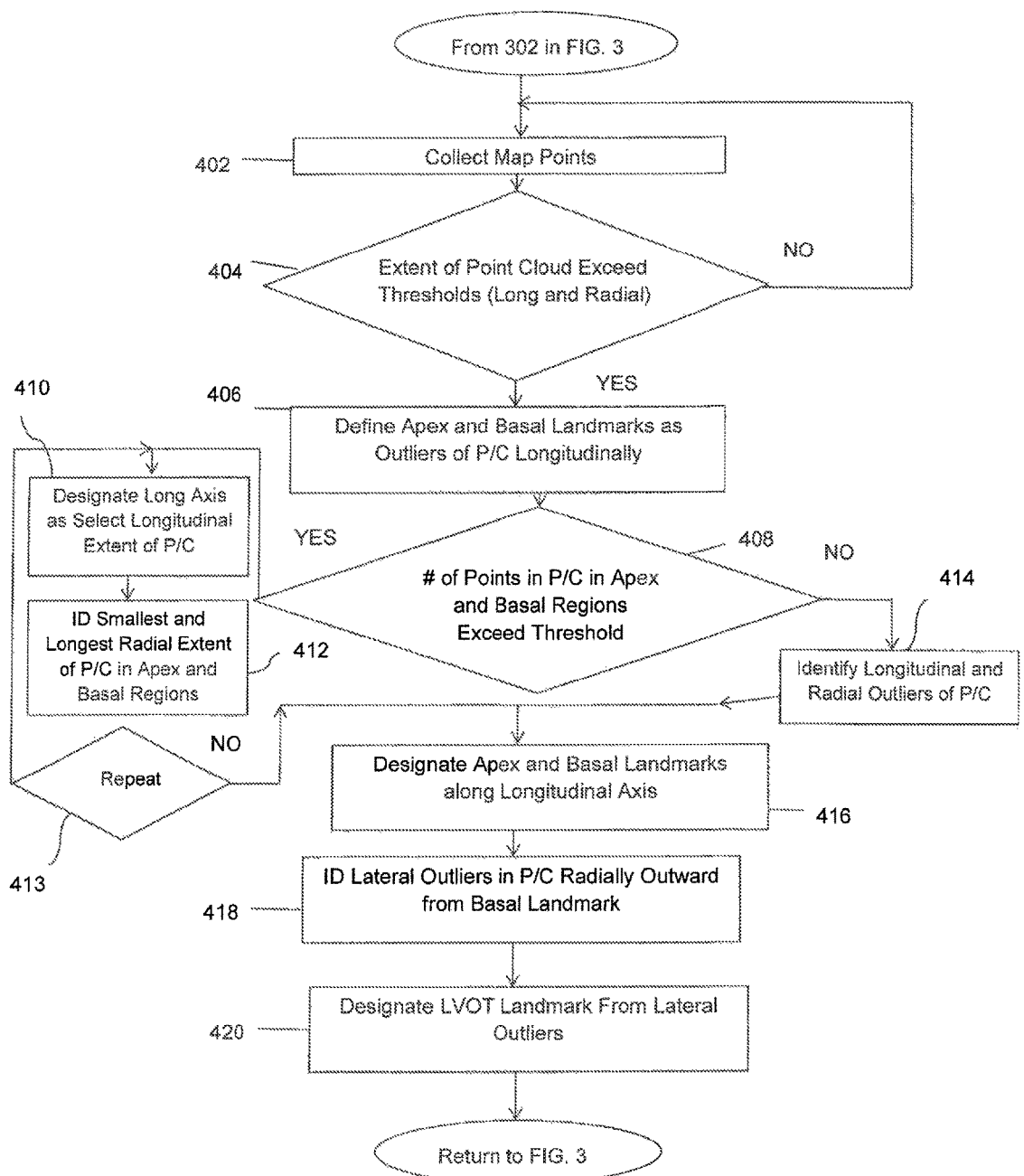
FIG. 4 illustrates a method for automatically designating landmarks in accordance with embodiments.

FIG. 4 illustrates a method for automatically designating landmarks in accordance with an embodiment. As explained hereafter, the method of FIG. 4 includes operations for a computer implemented analysis of the ROI data set. The computer implemented analysis includes identifying and apical and region and radial regions of the ROI data set. The computer implemented analysis identifies and apical data outlier that is located approximate to the apical in the region and identifies a lateral data outlier that is located proximate to at least one of the radial region. The analysis then designates the apical and basal landmarks based on the apical and radial data outliers.

Optionally, the computer implemented analysis may designate apical and basal landmarks relative to a longitudinal axis extending through the ROI data set. The analysis identifies a circumferential data outlier that is located laterally, relative to the longitudinal axis, at an outer extent of the ROI data set. The analysis designates a circumferential landmark based on the circumferential data outliers.

At 402, map points are collected as explained above in connection with FIG. 3.

At 404, a distribution or extent of the map points is analyzed to determine whether the distribution of the ROI data set exceeds one or more spatial thresholds. For example, the threshold may represent select (e.g., minimum) lateral and/or longitudinal dimensions for which the ROI data set map points should be distributed before a satisfactory amount of data exists to perform the spatial analyses described herein. When, it is determined that the ROI data set is not yet distributed sufficiently, longitudinally and/or laterally, to exceed the corresponding thresholds, flow returns to 402. When a sufficient extent/distribution of data points in the ROI data set is collected, flow moves to 406.

At 406, the method identifies spatial outliers of the ROI data set. The term outlier generally refers to one or more data points that are located at or proximate an outer boundary of the ROI data set. The ROI data set may exhibit various shapes based on the shape of the region of interest, the locations where data points are collected and the like. For example, the ROI data set may exhibit a conical shape, an "egg" shape, a spherical shape, a tubular shape and the like. With a conical shape, a small portion of the data points are located at the apex, while other portions of the data points are located along the peripheral boundaries or perimeter of the conical shape. A portion of the data points is located along the base boundary of the conical shape. In the example of a conical shape, the outlier data points represent one or more data points proximate the apex, the sides and the base perimeter or boundary. The outliers may not include the outermost data points such as when an error data point exists that is separated or decoupled from the remaining data points. For example, the method may utilize a spatial filter to remove data anomalies or irregularities that are spaced beyond a select spatial coupling threshold. For example, the outlier may be determined as an average or centroid for a cluster of data points at an outermost boundary of the majority of the data points, excluding anomalies.

At 406, the method defines an apical landmark and a basal landmark based on the spatial outliers of the ROI data set. The apical landmark may be designated as the point at which the ROI data set outliers extend furthest longitudinally in the apical direction. The basal landmarks maybe designated as laterally opposed points at which the ROI data set outliers radially extend the furthest transversely in a direction orthogonal to the longitudinal axis.

At 408, the method determines which of various alternative analyses are appropriate. At 408, it is determined whether the total number of map points in the ROI data set exceeds a post hoc threshold. When the extent of the ROI data set does not exceed the threshold, flow moves two 410. Otherwise, flow moves to 414.

The operations at 410-413 are performed iteratively, as the ROI data set initially (as determined at 408) is not sufficient to utilize (or "rely on") initial data points classified as the outliers. Instead, the operations at 410-413 repeatedly analyze the shape of the ROI data set that is created as the mapping tool(s) is(are) roved around in/over the anatomy of interest. The landmarks are then continuously and dynamically updated and the accuracy improved as the ROI data set is populated over time during the length of the procedure. In the case of endocardial mapping of the LV, for example, the initial "guess" can be obtained when the longitudinal extent of the ROI data set reaches a pre-defined threshold such as 30 mm and the radial extent reaches another pre-defined threshold such as 20 mm. In that case, the initial apex and basal landmarks are defined as the two extremes of the cloud. The LVOT is then landmarked as the sample point with the largest distance away from the defined long-axis, as long as it is larger than the pre-defined threshold of 20 mm for example. As data collection continues within the LV, the landmarks are updated, improving the accuracy of the automated process. The landmarks can be automatically finalized when the updated locations of the landmarks do not change more than a pre-defined threshold (e.g. 1 mm) over time with additional samples of the ROI data set. At this point, the user can be notified that no additional samples are necessary for anatomical landmarking.

At 410, the method identifies a current longitudinal extent of the ROI data set and designates the longitudinal axis to extend through the select current longitudinal extent of the ROI data set. At 412, the method identifies the current smallest and largest radial extent of the ROI data set in the apical region and in the basal region, respectively. The ROI data set is expected to have a small radial distribution or extent in the apical region, and a large radial extent or distribution in the basal region. The degree of the large and small radial distributions may be determined relative to one another, relative to reference longitudinal and lateral median distributions and the like. By identifying the largest and smallest distributions of the ROI data set, the method identifies regions that have a high probability of corresponding to the apex and basal regions of the RV, LV or other region of interest.

At 413, the method determines whether a sufficient amount of point data has been collected. The determination at 413 may be automatic or manually designated. When more point data is to be collected, 410 and 412 are repeated (as more data is collected), thereby iteratively updating the longitudinal line and radial extent of the ROI data set. When, at 413, it is determined that a sufficient amount of point data has been collected, flow moves to 416.

Returning to 404, flow moves to 414 when the method determines that a sufficient number of map points exist to directly identify the outliers based on the map points furthest from a central or centroid region of the ROI data set. At 414, the method identifies the longitudinal and paired radial outliers of the ROI data set. At 414 and 412, the paired radial outliers correspond to opposed boundaries that are coupled to a main body of the ROI data set in an expected peripheral shape or envelope. For example, when the region of interest is generally conical in shape, at 414 and 412, the method designates, as radial outliers, map points (or clusters of map points) that are located generally equal distances in opposite directions from a longitudinal axis or centroid of the ROI data set. Additionally or alternatively, the radial outliers also may be identified based on an amount of coupling or continuity exhibited relative to map points in adjacent peripheral regions of the ROI data set. Additionally or alternatively, other criteria may be used to exclude map points from other anatomical regions of the heart (e.g., to exclude map points from the LVOT).

At 416, the method designates the apical and basal landmarks. For example, the apical landmark is designated to correspond to the longitudinal outlier. When the longitudinal outlier represents a cluster of points, the apical landmark may be designated as the average, center or an outer edge of the cluster, or some other point based on the cluster. To define the basal landmark, a line may be drawn between the basal radial outliers to denote the plane of the base. A longitudinal line is then projected from the apical landmark perpendicular to the base plane. The point of intersection between the longitudinal line and the base plane represents the basal landmark.

At 418, the method searches for a cluster of map points located in a non-uniform position relative to the conical (or other uniform) shape of the region of interest. When the region of interest is the LV or RV, a left or right ventricular outflow track (LVOT or RVOT) exists that is located at a point along the circumference of the LV or RV. Map points collected at the LVOT or RVOT appear as a cluster that is spherical or some other expected shape that forms a deviation or irregularity in the otherwise conical shape of the LV or RV. At 418, the method seeks to locate the LVOT or RVOT by identifying the cluster irregularity.

At 420, the method designates a LVOT or RVOT landmark based on the irregularity cluster identified in 418. The LVOT landmark may be located at an outer edge, a center or elsewhere on the irregularity cluster.

In the case of a post-hoc analysis, as at 414, the automatic process described herein is applied to the entire ROI data set without the need for iterative updates. In this case, the largest longitudinal extent of the cloud is found and the long axis is drawn. The apex is then defined as the extreme with the smallest radial extent in the vicinity and the basal centroid as the opposite end of the long axis. The circumferential landmark is again automatically detected as the point with the largest distance away from the basal centroid in the basal region of the ROI data set. Thereafter, flow returns to FIG. 3.

Figure 5:
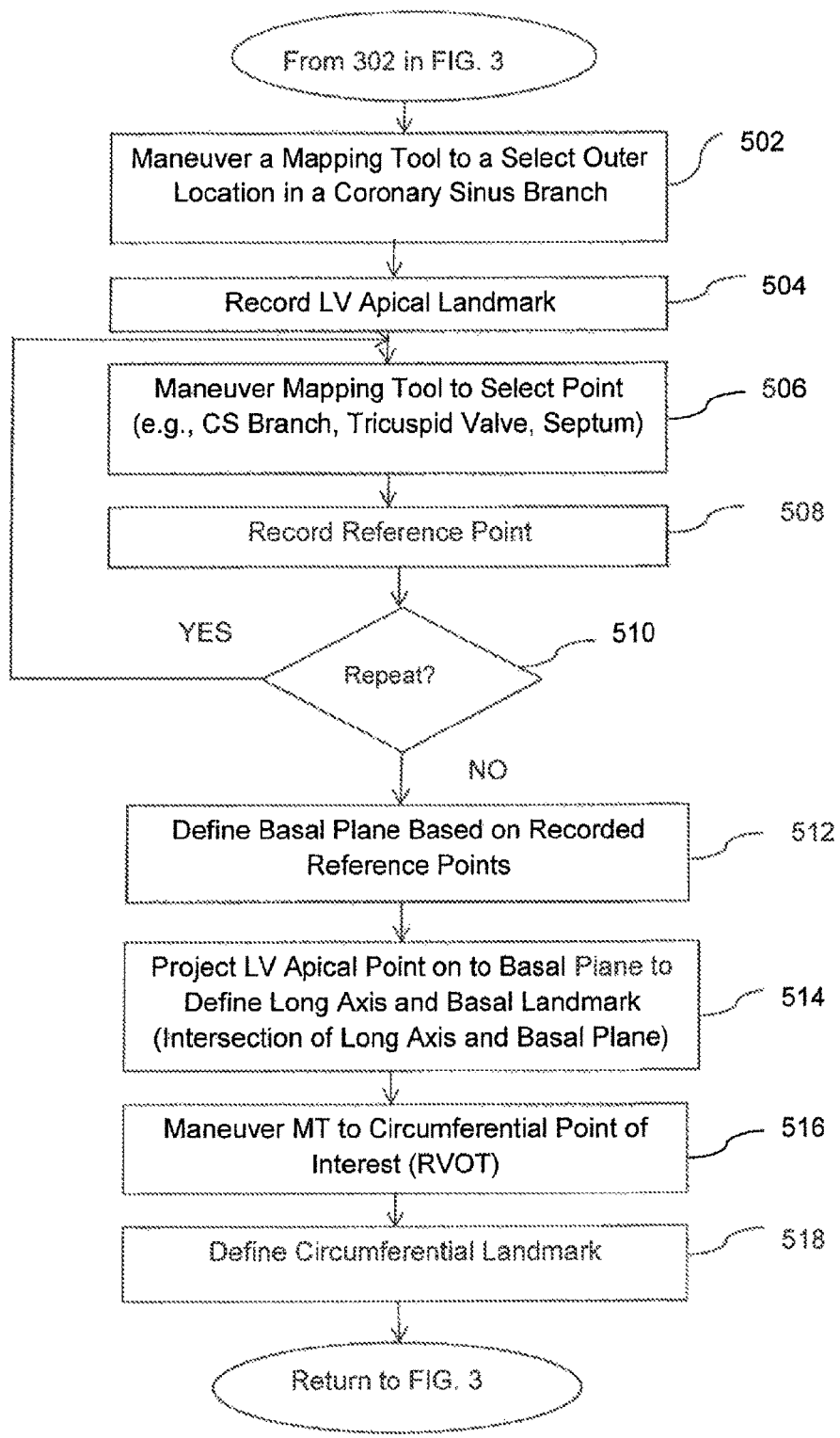
FIG. 5 illustrates a user-guided method for designating anatomical landmarks in accordance with embodiments.

FIG. 5 illustrates a user-guided method for designating anatomical landmarks in accordance with an alternative embodiment. At 502, a physician maneuvers a mapping tool to a select outer location in a coronary sinus branch.

At 504, the system records a left ventricular apical landmark in connection with the select outer location in the coronary sinus branch. The LV apical landmark may be defined at the deepest coronary sinus branch reachable. Alternatively, the LV apical landmark may be designated as a point located a predetermined distance (and predetermined trajectory) beyond the end of the mapping tool. Designating the LV apical landmark to be beyond the end of the mapping tool may be desirable when the patient's vein structure prevents the mapping tool from reaching the LV apex (or moving to a point in close proximity to the LV apex).

At 506, the physician maneuvers the mapping tool to a select point within the heart. For example, the physician may locate the mapping tool at a select location of interest on the tricuspid valve, such as near the right ventricular free wall or near the septum. Once the mapping tool is positioned at the select location, the user enters an input indicating that the tool is at a select location.

At 508, the system records the reference point associated with the select point designated in 506.

At 510, the method determines whether additional reference points are needed. For example, the user may be prompted. Alternatively, when seeking to define the basal plane, the method may be configured to collect two or preferably three reference points. Accordingly, the operations at 506-510 are repeated at least three times to collect a desired number of reference points. During each iteration through 506-510, the physician adjusts the position of the mapping tool until located at a select location. For example, the physician may first locate the mapping tool in the proximal region of the coronary sinus branch to be recorded as one reference point. Next or previously, the user may locate the mapping tool at a reference point along the septum and then along the RV free wall.

At 512, the method defines the basal plane based on the recorded reference points. For example, the basal plane may be defined based on a point at the RV free wall, a point at the septum and a point in the proximal end of the coronary sinus. Optionally, other reference points may be used to define the basal plane. For example, epicardial reference points may be recorded by maneuvering the mapping tool through one or more veins along an exterior of the heart in the region of the basal area of the chamber of interest. Optionally, more or fewer than 3 reference points may be used to define the basal plane.

At 514, the method projects an orthogonal line from the LV apical point on to the basal plane to define the long axis. The point at which the long axis intersects the basal plane is defined as the basal landmark.

At 516, the physician maneuvers the mapping tool to a circumferential point of interest such as a point in the left or right ventricular outflow tract (LVOT or RVOT).

At 518 the method defines a circumferential landmark associated with the LVOT or RVOT. As explained herein, the circumferential landmark is used to define a circumferential origin when converting map points from the Cartesian coordinate system to a cylindrical coordinate system. The tertiary circumferential landmark in this case can be an RVOT landmark obtained by maneuvering a mapping tool near the RVOT which still indicates the anteroseptal wall. Alternatively, a septal landmark can be used by detecting a His bundle potential along the RV septum that would indicate the circumferential location of the septal wall.

In the case of a CRT implant when endocardial mapping may not be used, the landmarking strategy of FIG. 5 may be used during epicardial mapping in the coronary sinus branches or other vein structure. Thereafter, flow returns to FIG. 3.

Figure 6:
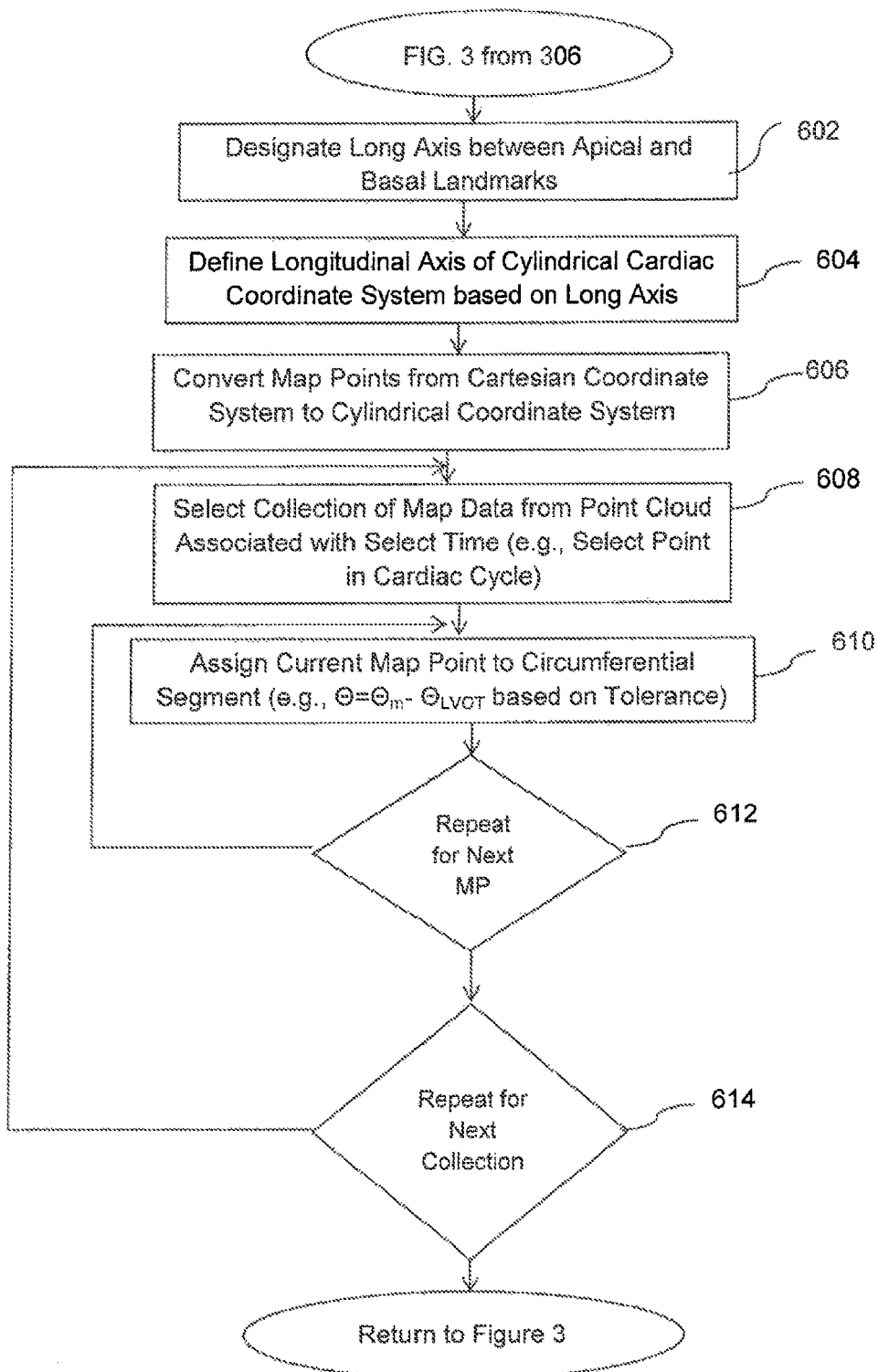
FIG. 6 illustrates a process for calculating circumferential segment boundaries and assigning map points to circumferential segments in accordance with embodiments.

FIG. 6 illustrates a process for calculating circumferential segment boundaries and assigning map points to circumferential segments in accordance with embodiments herein. FIG. 6 represents one implementation of the operations at 306 and 308 in FIG. 3.

At 602, the process designates the long axis to extend between the apical and basal landmarks. The apical and basal landmarks may have been designated manually or automatically. For example, the processes of FIGS. 4 and 5 represent non-limiting examples of manual and automatic methods for designating the apical and basal landmarks.

At 604, the method defines the longitudinal Z-axis of a cylindrical coordinate system to correspond to the long axis denoted in 602. The origin of the cylindrical coordinate system may be located at various points. For example, the origin of the cylindrical coordinate system maybe located at the apical landmark. The coordinate system is oriented with the circumferential reference axis (theta equal zero) aligned with the circumferential axis extending between the basal and circumferential landmark.

Optionally, the origin maybe located at another point defined based on the basal, apical and circumferential landmarks. The circumferential axis may also be oriented at a different position, not in line with the circumferential landmark.

At 606, the map points are converted from Cartesian coordinates to the cylindrical coordinate system. Various techniques maybe used for transforming between the Cartesian and cylindrical coordinate systems. For example, the landmarks maybe used to construct a set of transformation models through which the map points are processed to transform between the desired three dimensional coordinates systems.

While embodiments herein are described in connection with conversion from Cartesian to cylindrical coordinate systems, the present disclosure is not limited thereto. Instead, alternative base coordinate systems may be used instead of the Cartesian coordinate system. For example, the map points may be originally constructed in the spherical coordinate system or the cylindrical coordinates system. When the original map points are collected in the spherical coordinate system, a transformation may not be utilized. When the original map points are collected in the cylindrical coordinates system, the operations at 606 maybe omitted. Optionally, the map points may be converted to an alternative coordinate system other than the cylindrical coordinate system. For example, the map points may be transformed to the spherical, polar or another system. The end transformation coordinate system may be selected in part based upon the anticipated overall structure of the region to be mapped. For example, it may be desirable, when mapping the RA or LA, to use a spherical coordinate system.

At 608, the method selects a collection of the map points from the ROI data set. The collection is associated with a select point in time at which the map points were collected. As explained herein, map points are collected throughout the cardiac cycle. It may be desirable at 608 to select a collection of map points for a particular point in the cardiac cycle. For example, a collection of maps points maybe selecting that correspond to the peak of the R waves.

At 610, a current map point from the current collection of map points is analyzed and assigned to a circumferential segment. When mapping the LV, the left ventricular wall may be virtually separated into a number of segments (E.g. six segments), such as the anteroseptal, anterior, lateral, septal, inferior, and posterior wall segments. Each map point is assigned to a corresponding segment. Optionally, a tolerance maybe added in connection with map points near segment boundaries. When a map point falls within a tolerance of a segment boundary, the map point may be assigned to both segments. Alternatively, when the map point falls within a tolerance to segment boundary, the map point may be assigned to a segment designated to have priority. Other options exist for assigning map points located proximate to segment boundaries, and falls within the scope of the embodiments described herein.

For example, at 610, the circumferential location of a map point and the circumferential (LVOT) landmark may be considered at a pre-defined point in the cardiac cycle such as diastole at the peak of the R-wave and defined as $\theta_m$ and $\theta_{LVOT}$, respectively. The method defines $\theta = \theta_m - \theta_{LVOT}$ and defines a tolerance level (for example $\pi/36$) on either side of each segmental boundary. The tolerance level defines the shared region between adjacent segments. Map points that fall within the tolerance level of the segment boundary are assigned to both adjacent segments. The assignment of circumferential walls is then as follows:

theta<=(pi/6+tolerance) & theta>(-pi/6-tolerance) % Anteroseptal
theta>=(pi/6-tolerance) & theta<(pi/2+tolerance) % Anterior
theta>=(pi/2-tolerance) & theta<(5*pi/6+tolerance) % Lateral
theta<=(-pi/6+tolerance) & theta>(-pi/2-tolerance) % Septal
theta<=(-pi/2+tolerance) & theta>(-5*pi/6-tolerance) % Inferior
abs(theta)>=(5*pi/6-tolerance) % Posterior In the case of a CRT implant, when a septal circumferential landmark is defined, the following assignments may be made instead:

theta<=(pi/6+tolerance) & theta>(-pi/6-tolerance) % Septal
theta>=(pi/6-tolerance) & theta<(pi/2+tolerance) % Anteroseptal
theta>=(pi/2-tolerance) & theta<(5*pi/6+tolerance) % Anterior
theta<=(-pi/6+tolerance) & theta>(-pi/2-tolerance) % Inferior
theta<=(-pi/2+tolerance) & theta>(-5*pi/6-tolerance) % Posterior
abs(theta)>=(5*pi/6-tolerance) % Lateral At 612, the process determines whether additional points exist in the current collection. When additional points exist, flow returns to 610 in order that the next map point is assigned to a segment. The assignment operation 610 is repeated for each map point in the collection.

At 614, the method determines whether additional collections of map points should be processed for segment assignment. For example, it may be desirable to separately assign segments for multiple points along the cardiac cycle. For example, collections may be assigned in connection with multiple user defined time points along the cardiac cycle, or at select events within the cardiac cycle. Thereafter, flow returns to FIG. 3.

Figure 7:
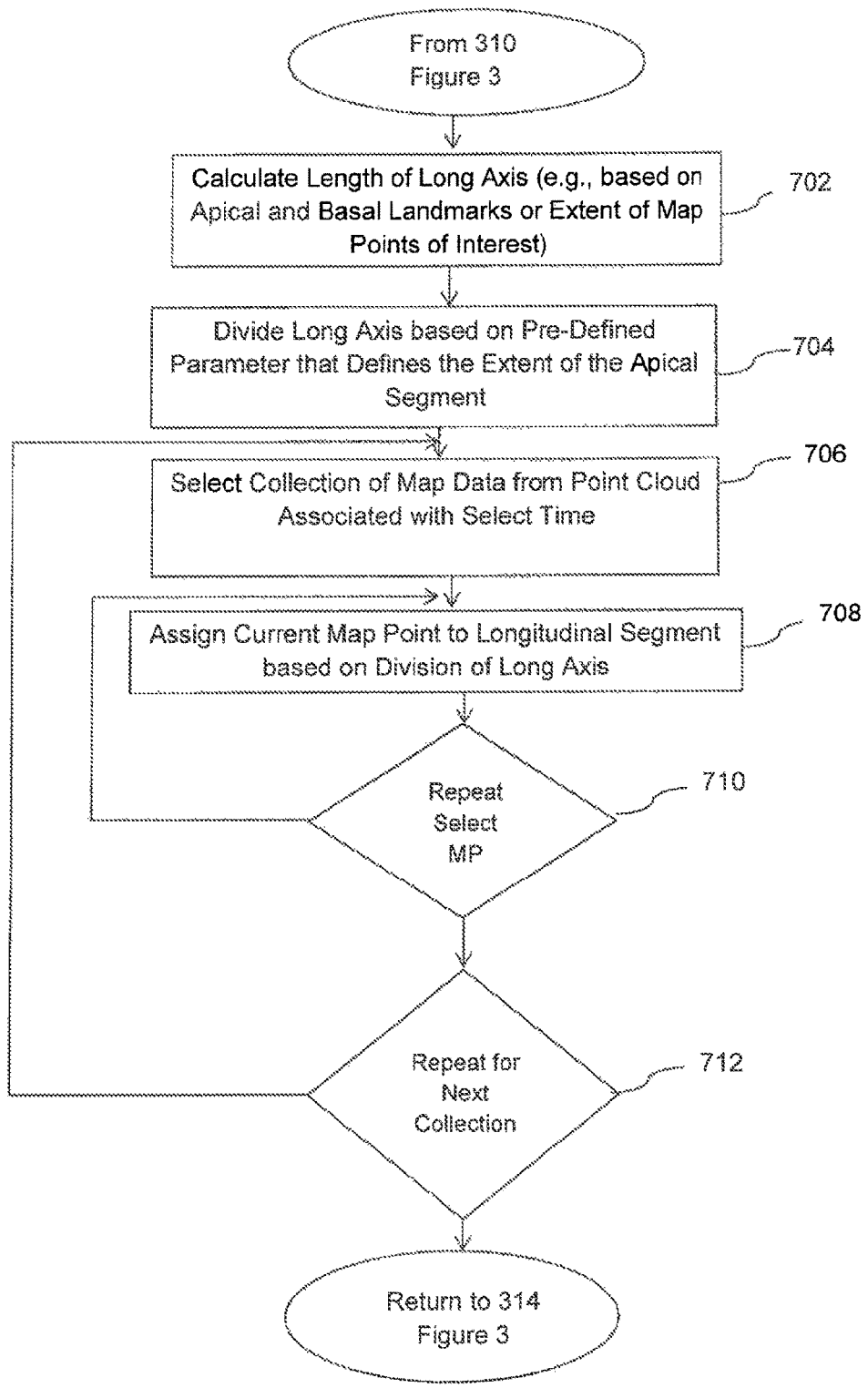
FIG. 7 illustrates a process for calculating longitudinal segment boundaries and assigning map points to longitudinal segments in accordance with embodiments.

FIG. 7 illustrates a process for calculating longitudinal segment boundaries and assigning map points to longitudinal segments in accordance with embodiments herein. FIG. 7 represents one implementation of the operations at 310 and 312 in FIG. 3.

At 702, the method calculates the length of the long axis based on the distance between the apical and basal landmarks. Optionally, the length may be calculated based on the extent of the map points of interest.

At 704, the method divides the long axis in longitudinal segments based on predefined parameters. For example, the predefined parameters may designate a number of longitudinal segments to be used, a length of each longitudinal segment and the like. The longitudinal segments may be equal in length and evenly spaced along the long axis. Optionally, one or more of the longitudinal segments may have a different longitudinal length relative to the other longitudinal segments.

At 706, the method selects a collection of the map points from the ROI data set (e.g., the same collection as at 608 in FIG. 6). The collection is associated with a select point in time at which the map points were collected. It may be desirable at 706 to select a collection of map points for a particular point in the cardiac cycle. For example, a collection of maps points may be selected that correspond to the peak of the R waves.

At 708, a current map point from the current collection of map points is analyzed and assigned to a longitudinal segment. When mapping the LV, the left ventricular wall may be virtually separated into a number of segments (e.g., three segments), such as the apical, middle and basal wall segments. Each map point is assigned to a corresponding segment. Optionally, a tolerance maybe added in connection with map points near segment boundaries. When a map point falls within a tolerance of a segment boundary, the map point may be assigned to both segments.

The automatic longitudinal assignment is accomplished as follows by considering the longitudinal coordinate of the map point of interest (Z) at a pre-defined point in the cardiac cycle such as the R-wave. The apical portion (AP) parameter is defined which determines the extent of the apical segments. A longitudinal tolerance can also be incorporated to allow for some flexibility as follows:

Z<=L/AP+tolerance % Apical
Z>L/AP-tolerance & Z<=((AP+1)*L)/(2*AP)+tolerance % Mid-ventricular
Z>((AP+1)*L)/(2*AP)-tolerance % Basal At 710, the process determines whether additional points exist in the current collection. When additional points exist, flow returns to 708 in order that the next map point is assigned to a segment. The assignment operation 708 is repeated for each map point in the collection.

In general, the operation at 712 may be omitted and the process of FIG. 7 only performed for one collection (e.g., when the map points are at one location). Optionally, at 712, the method determines whether additional collections of map points should be processed for segment assignment. For example, it may be desirable to repeat segment assignment when at multiple points along the cardiac cycle. The separate assignments may be compared, combined, or averaged to obtain a final assignment. Thereafter, flow returns to FIG. 3.

In accordance with the processes of FIGS. 3-7, a set of map points is automatically assigned to 18 different segments of the LV.

Figures 8A, 8B, 8C:
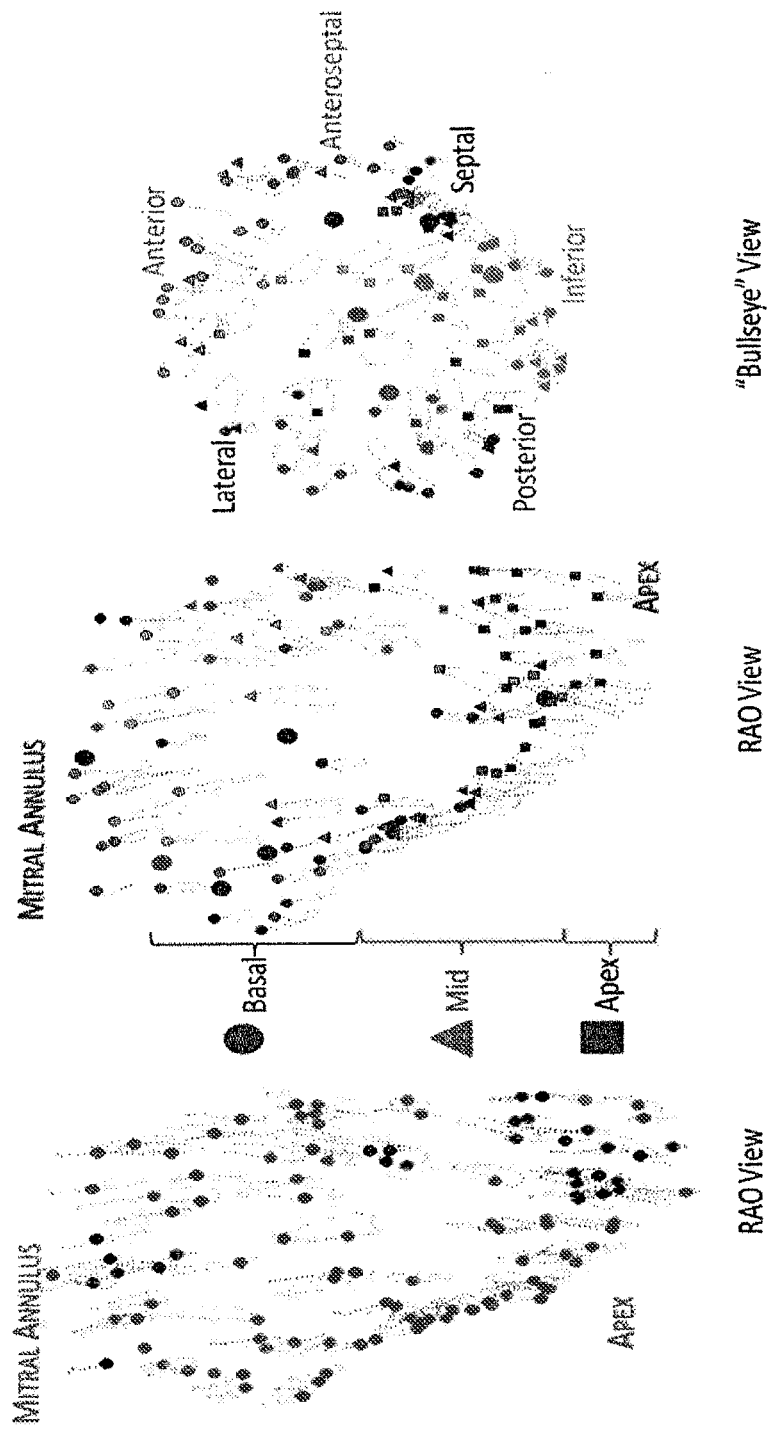
FIG. 8A illustrates a set of endocardial map points shown with their respective trajectories before segmentation with manual anatomical markers at the mitral annulus and the apex in accordance with embodiments.
FIG. 8B illustrates the same set of endocardial map points as in FIG. 8A, but segmented automatically in the longitudinal direction with the basal points shown as circles, mid-ventricular points as triangles, and apical points as squares in accordance with embodiments.
FIG. 8C illustrates the same set of endocardial map points as in FIG. 8A, but segmented circumferentially in a bullseye plot with different colors showing the different wall segments in accordance with embodiments.

FIG. 8A illustrates a set of endocardial map points shown with their respective trajectories before segmentation with manual anatomical markers at the mitral annulus and the apex.

FIG. 8B illustrates the same set of endocardial map points as in FIG. 8A, but segmented automatically in the longitudinal direction with the basal points shown as circles, mid-ventricular points as triangles, and apical points as squares.

FIG. 8C illustrates the same set of endocardial map points as in FIG. 8A, but segmented circumferentially in a bullseye plot with different colors showing the different wall segments. The information in FIGS. 8A-8C may be displayed to the user throughout the processes described herein.

Figure 9:
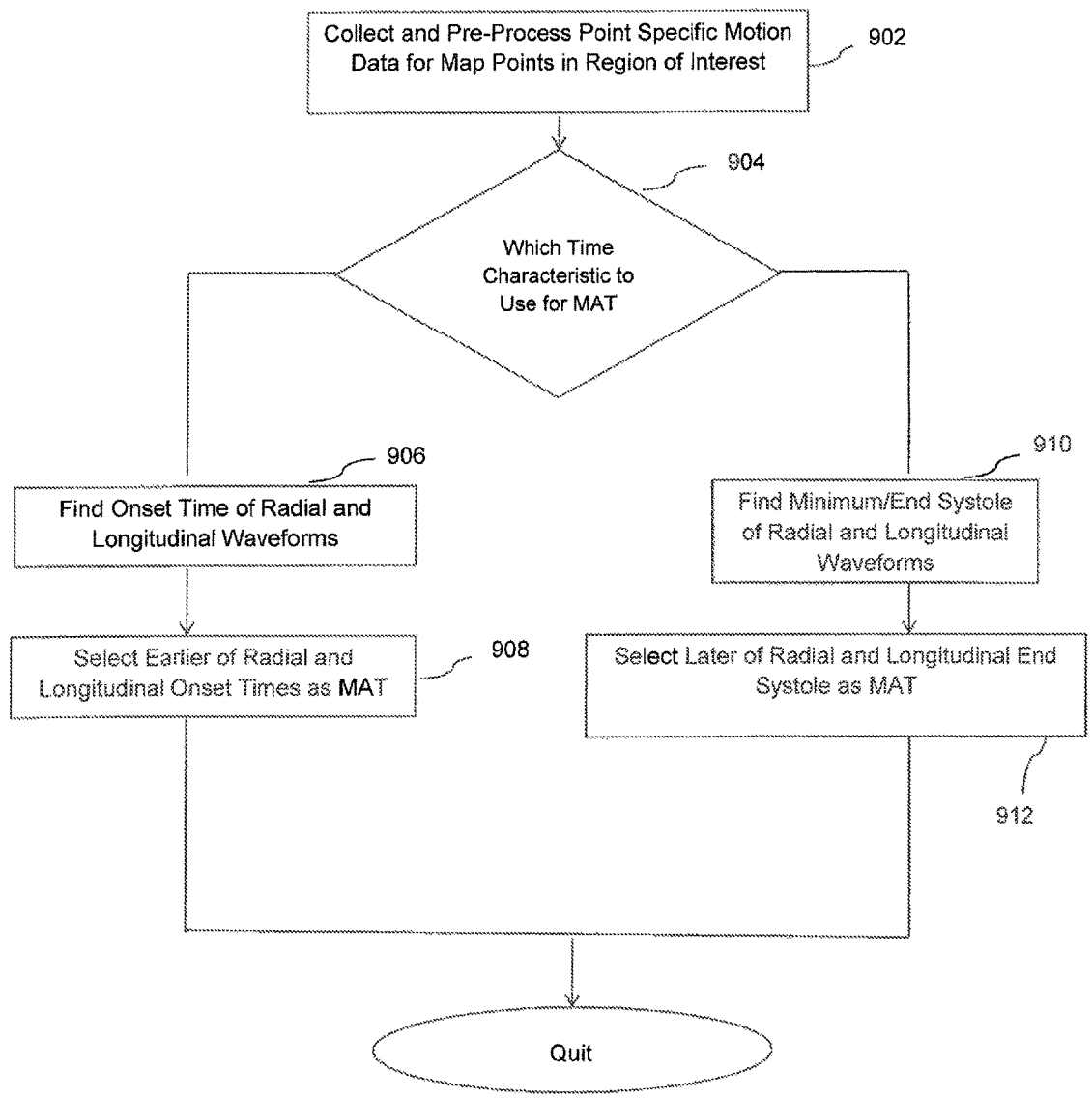
FIG. 9 illustrates a process for selecting between different motion components for mapping mechanical activation in accordance with embodiments.

FIG. 9 illustrates a process for selecting between different motion components for mapping mechanical activation.

At 902, the method collects and preprocesses point specific (PS) motion data for map points in the region of interest. The PS motion data is preprocessing such as compensating for patient movement, correcting for angulation and position of the image acquisition system, correcting for respiratory movement. Further, at 902, the PS motion data is converted to the patients cardiac coordinate system and decomposed into radial, longitudinal, and circumferential vectors or components. Further, at 902, the PS motion data is analyzed and filtered such that the PS motion data is associated with select points in time, such as select points or phases in the cardiac cycle. At 902, the method may ensemble average and rotate the motion data. Alternatively, the method may select desired PS motion data for a select cardiac cycle.

The PS motion data associated with each map point includes components associated with movement along different directions. For example, the motion may be characterized by directional components associated with movement having radial, longitudinal, and circumferential displacement. Each map point exhibits movement in at least one (and generally in all three) directions of displacement during a cardiac cycle. The examples provided herein describe the cases of evaluating radial and longitudinal motion components. However, it is understood, that the present disclosure includes evaluation of mechanical activation time based on the circumferential component of movement, as well as any two components out of the three components, and as well as based on all three components of movement.

Figure 10A:
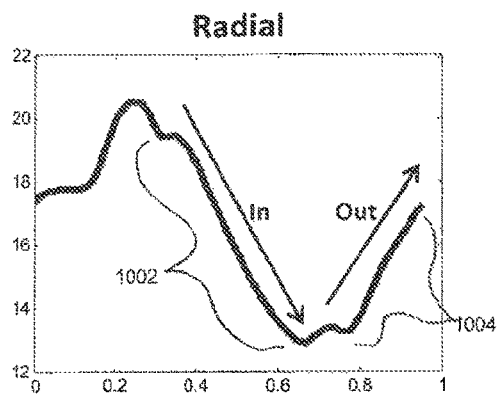
FIGS. 10A and 10B illustrate examples of radial and longitudinal motion waveforms, respectively, associated with PS motion data collected for a select map point in accordance with embodiments.
Figure 10B:
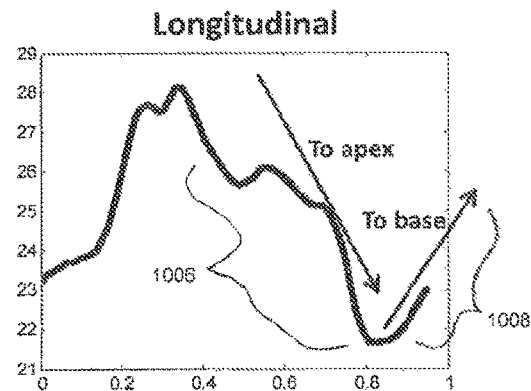

FIGS. 10A and 10B illustrate examples of radial and longitudinal motion component waveforms, respectively, associated with PS motion data collected for a select map point. As shown in FIG. 10A, the radial motion waveform exhibits radial inward displacement (e.g., toward a center of the chamber/region of interest) along the waveform segment denoted at 1002 and radial outward displacement (e.g., away from a center of the chamber/region of interest) along region waveform segment at 1004. As shown in FIG. 10B, the longitudinal motion waveform exhibits extension displacement (e.g., toward an apex of the chamber/region of interest) along the waveform segment denoted at 1006 and longitudinal contractive displacement (e.g., toward a base of the chamber/region of interest) along region waveform segment at 1008.

Figure 11A:
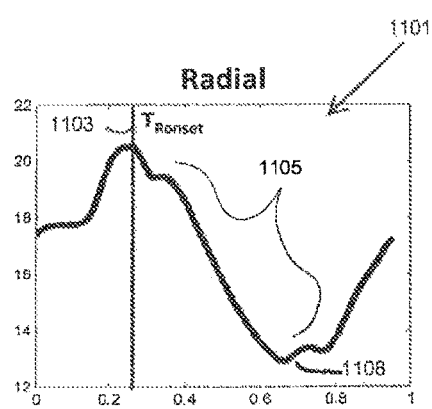
FIGS. 11A-11D show four ways of annotating motion waveforms to find time of mechanical activation in accordance with embodiments.
Figure 11B:
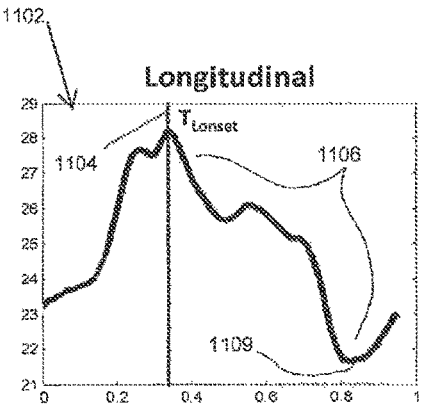
Figure 11C:
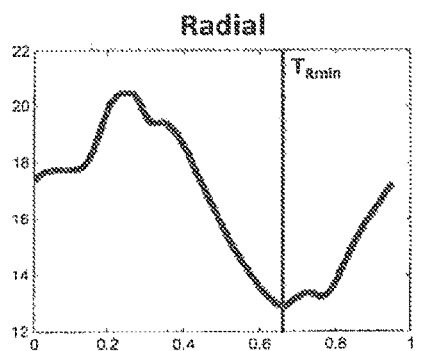
Figure 11D:
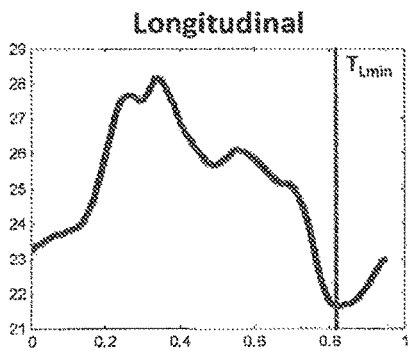

FIGS. 11A-11D show four ways of annotating motion waveforms to find time of mechanical activation. In FIGS. 11A and 11B, the method finds the time at which systole begins, which corresponds to the onset of inward motion in the radial motion waveform (FIG. 11A, $T_{Ronset}$) and the onset of movement toward the apex in the longitudinal motion waveform (FIG. 11B, $T_{Lonset}$). The second method (FIGS. 11C and 11D) finds when systole ends, which corresponds to the time when radial waveform reaches its minimum (FIG. 11C, $T_{Rmin}$) and the longitudinal waveform reaches its minimum (FIG. 11D, $T_{Lmin}$). Optionally, the method may find a time when the waveform reaches a percentage of the minimum.

Returning to FIG. 9, at 904, the method determines what timing characteristic of the waveform is to be used to determine the MAT. The decision at 904 is utilized as the motion at different map points is a combination of different directional motion components. A map point may begin moving in only one direction and then start moving in another direction instead of, or in addition to the first direction. For example, the map point may start moving only in the radial direction and then move (solely or in addition) in the longitudinal direction. Similarly, a map point may reach a furthest radial displacement position at one point in time and a furthest longitudinal displacement position at another point in time. Therefore, the method of FIG. 9 examines both directions and utilizes the directional component that exhibits earlier movement (when looking for onset of systole) and utilizes the direction component that exhibits later movement (when looking for end of systole).

At 904, the method determines whether the MAT is to be determined based on onset or end of systole. When the MAT is based on systole onset, flow moves to 906. When the MAT is based on end systole, flow moves to 910.

At 906, with reference to FIGS. 11A and 11B, the method analyzes the radial and longitudinal motion waveforms 1101 and 1102 to find the peaks of the waveforms representative of the onset of radial and longitudinal movement (as denoted at 1103 and 1104). The waveform segments 1105 and 1106 represent contraction at the map point in the region of interest in the radial and longitudinal directions.

At 908, the onset times of the radial and longitudinal waveforms (determined at 906) are then compared to identify the one earlier in time. The method selects the earlier of the radial and longitudinal onset times at 908 as the mechanical activation time for the current map point.

Returning to 904, when the method determines that end systole is to be used to determine the MAT for each map point, flow moves to 910.

At 910, with reference to FIGS. 11A and 11B, the method analyzes the radial and longitudinal motion waveforms 1101 and 1102 to find the minimum of the waveforms representative of the end of radial and longitudinal movement (as denoted at 1108 and 1109). Optionally, another characteristic (besides the minimum) of the contraction waveform segments 1105 and 1106 may represent the end systole times.

At 912, the end times of the radial and longitudinal waveforms (determined at 910) are compared to identify the one later in time. The method selects the later of the radial and longitudinal end times at 912 as the mechanical activation time for the current map point.

It is understood that the operations at 906 or 912 are performed for each map point of interest in motion data collected at 902.

In accordance with FIG. 9, the method finds $T_{Ronset}$ and $T_{Lonset}$ from the two displacement traces and uses the earlier one to determine the time of mechanical activation onset for that map point. If end of systole is being used to find time of mechanical activation, the method finds $T_{Rmin}$ and $T_{Lmin}$ from the two displacement traces and uses the later one of the two to determine the time of mechanical activation for that map point.

Referring to FIGS. 11A and 11B, in this example, the method is using the onset of MAT for annotation. In the example of FIGS. 11A and 11B, the radial motion has an earlier time of onset than the longitudinal motion, and thus, the timing from the radial motion component would be used. In the example of FIGS. 11C and 11D, the time of maximum displacement (end systole) is used for annotation. In the case of FIGS. 11C and 11D, the longitudinal motion reaches a minimum later than the radial motion reaches a minimum, and thus the timing from the longitudinal component would be used.

Figure 12:
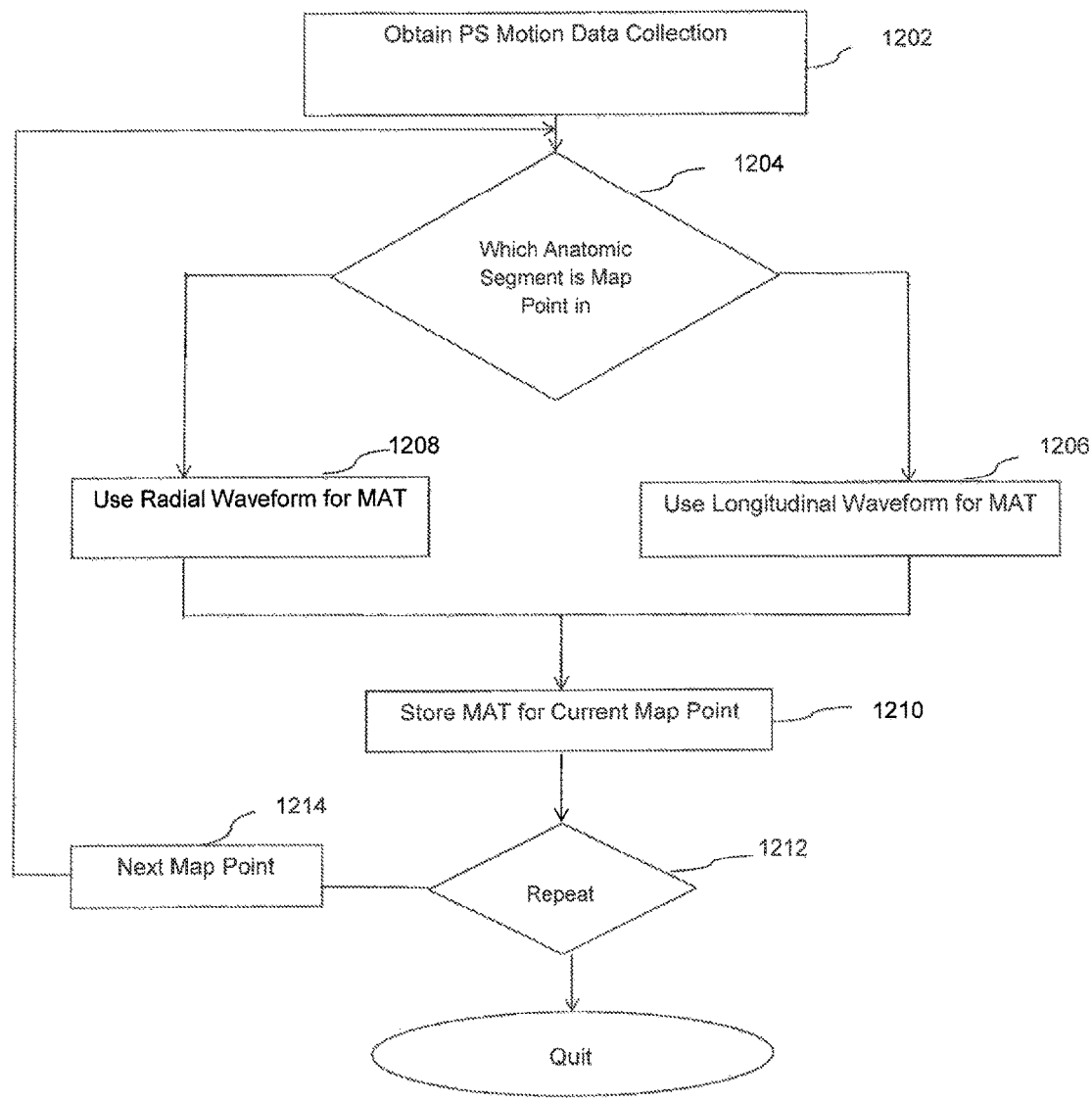
FIG. 12 illustrates an alternative process for selecting between motion components in accordance with embodiments.

FIG. 12 illustrates an alternative process for selecting between motion components in accordance with an embodiment. The selection of FIG. 12 is based on a location of the map point relative to the region of interest or a reference point. For example, map points located proximate to the base of the heart exhibit large longitudinal movement toward the apex. As a further example, map points close to the apex of the heart exhibit small longitudinal movement, but exhibit relatively moderate radial movement (relative to movement elsewhere about the heart).

At 1202, the PS motion data for a collection of map points is obtained.

At 1204, a current map point is selected and analyzed to determine, in which wall segment of the heart the current map point is located. As explained above in connection with FIGS. 3-8, the map points are segmented and assigned to wall segments. At 1204, the method determines whether the map point is in a wall segment for which motion is predominately in the radial or longitudinal direction. When motion is predominately in the radial direction, flow moves to 1208, and when motion is predominately in the longitudinal direction, flow moves to 1206.

At 1206, the method uses the longitudinal motion waveform associated with the current map point in the collection to identify the MAT. The MAT may be based on various characteristics of the waveform (e.g., the onset or end of systole segment of the motion waveform).

At 1208, the method uses the radial motion waveform associated with the current map point in the collection to identify the MAT. The MAT may be based on various characteristics of the waveform (e.g., the onset or end of systole segment of the motion waveform).

At 1210, the MAT value is stored for the current map point. At 1212, the method determines whether addition map points exist for which MAT values are to be determined. If so, flow moves to 1214, where the next map point is selected and flow returns to 1204, at which the next map point is analyzed to determine which motion component should be used to determine MAT.

Additionally or alternatively, at 1204, the method may determine which map points are located in a wall segment for which circumferential motion is a select indicator of MAT. In this example, a separate branch may occur from 1204 to an analysis of MAT based on circumferential motion waveforms.

In the embodiment of FIG. 12, the direction of the displacement waveform to be used for finding time of mechanical activation will depend on the location of the map point. For example, longitudinal displacement will be used to find time of mechanical activation for motion points that are in the basal and mid-ventricular segments of the heart and radial displacement will be used at the apical map points.

Figure 13:
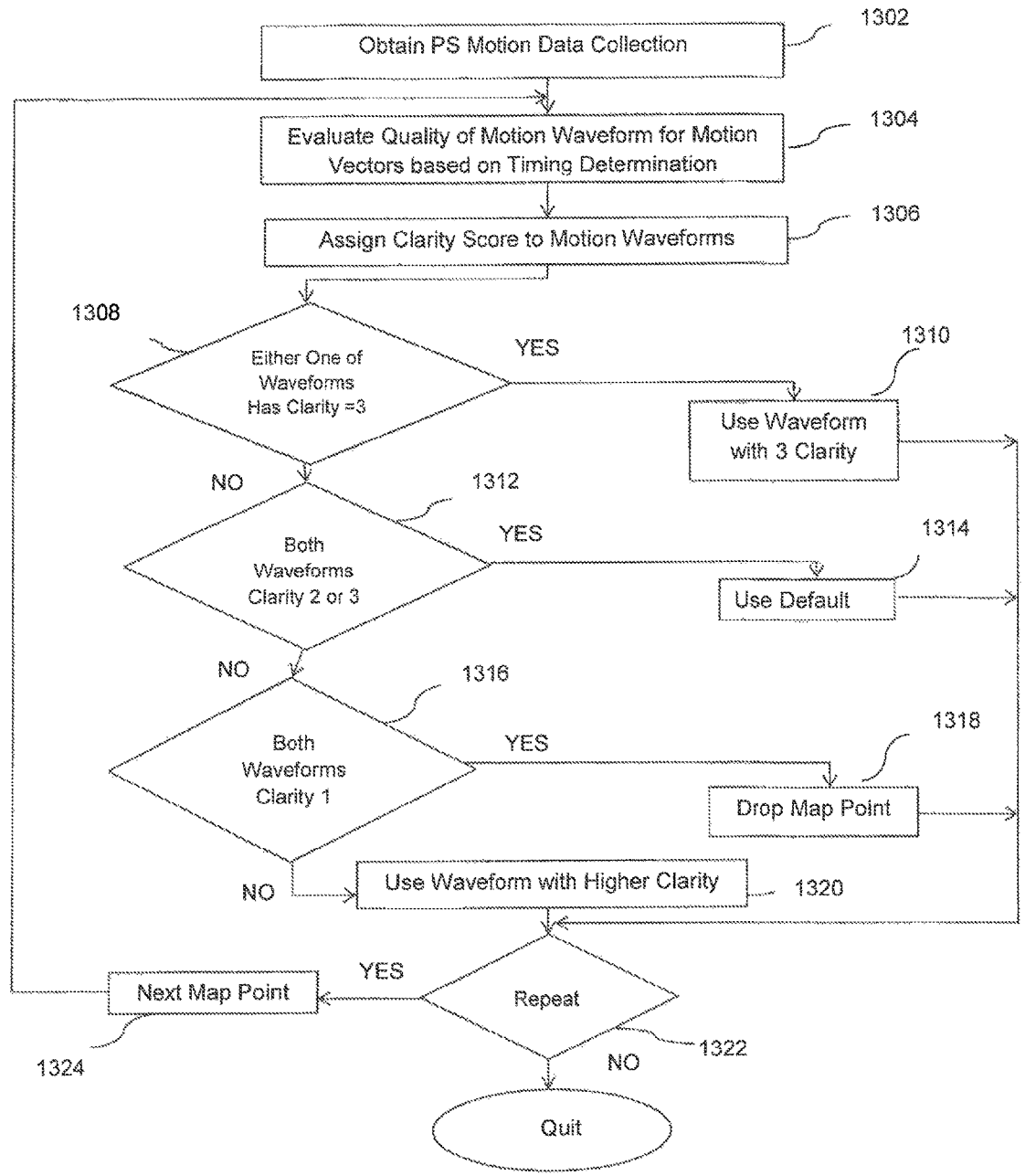
FIG. 13 illustrates an alternative process for selecting between motion components in accordance with embodiments.
Figure 14A:
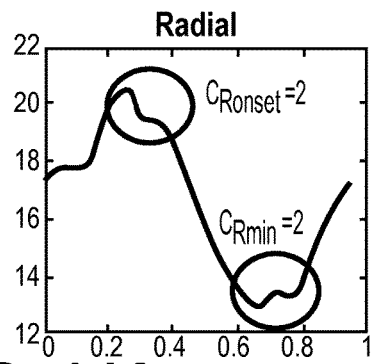
FIGS. 14A-D illustrate examples of component motion waveforms that may be analyzed for radial and longitudinal component motion in accordance with embodiments.
Figure 14A:
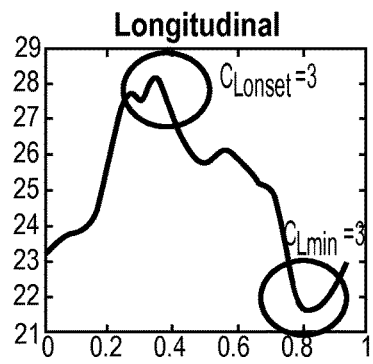
Figure 14B:
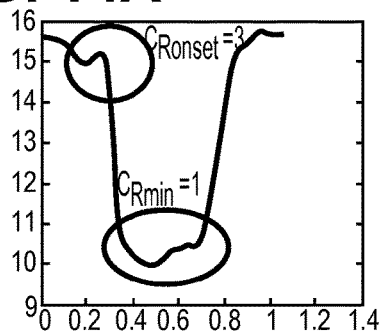
Figure 14B:
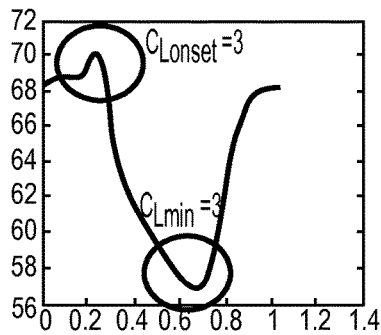
Figure 14C:
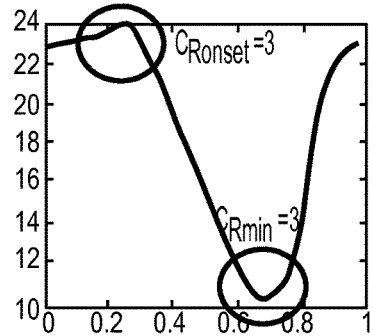
Figure 14C:
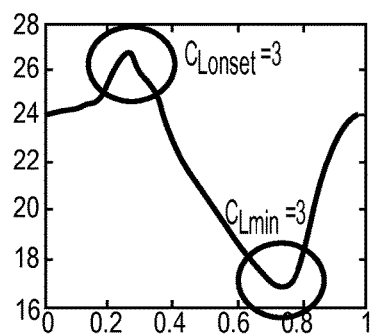
Figure 14D:
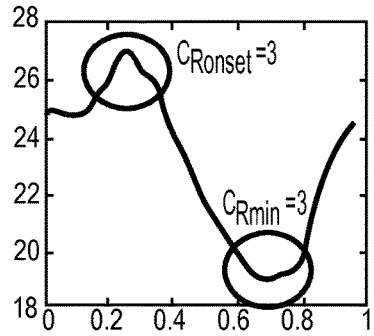
Figure 14D:
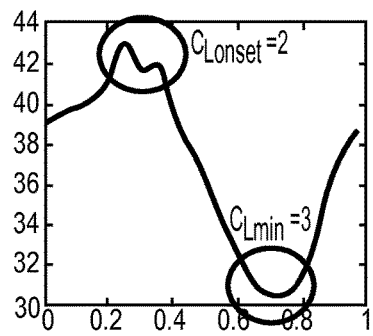

FIG. 13 illustrates an alternative process for selecting between motion components in accordance with an embodiment. The selection of FIG. 13 is based on a morphology of the motion waveforms associated with the motion components.

At 1302, a collection of PS motion data is obtained. The operations at 1304 to 1324 are repeated for each map point in the collection of PS motion data.

At 1304, the method evaluates the motion waveforms for the motion components associated with the current map point. For example, the radial, longitudinal and/or circumferential motion waveforms are analyzed. The analysis may include analyzing one or more characteristics of interest of each motion waveform, such as the angle of the waveform at select points, along select segment portions and the like. The characteristic of interest may include a presence of notches in a vicinity of onset and/or end systole. The characteristic of interest may represent a number of peaks/valleys, a number of changes in slope and the like.

At 1306, the method assigns a clarity score to each motion waveform. For example, a clarity score may be assigned such as 3=very clear, 2=somewhat clear, 1=not clear. As an example, when using the onset for timing determination, a clarity score may depend on the angle of the waveform at the onset and the presence of notches in the vicinity of the onset. A sharp angle (90-120 degrees) and absence of notches may yield a clarity score of 3 because it would be very easy to determine the time of onset. A less sharp angle (121-150 degrees) with or without a small notch may yield a clarity of 2, and either an obtuse angle and/or presence of one or more large notches may yield a clarity of 1.

As another example, when using time of maximum displacement to determine mechanical activation, the process may determine a clarity score based on other characteristics of the waveform.

The user may determine which directional component (radial, longitudinal and circumferential) of displacement will represent a default when all three or both radial and longitudinal directions have high quality waveforms. The default may be designated based on which directional component waveform exhibits higher clarity the majority of the time in the entire heart chamber. Alternatively, the default may be designated based on the location of the map point, as described above in connection with FIG. 12. Yet another option is to use principal component analysis for a given segment, wall, or entire heart chamber to determine which direction of motion is the more prominent direction and using that as the default. For each map point, the method calculates and assigns the clarity scores at 1306 of the radial and longitudinal displacement waveforms.

At 1308, the method reviews the clarity scores. If either one of the motion component waveforms (for the longitudinal and radial motion components) has a clarity of 3, flow moves to 1310 and the corresponding motion waveform having the high clarity score is used to determine the MAT for the current map point. Otherwise, flow moves to 1312.

At 1312, the method determines whether the longitudinal and radial motion waveforms were assigned clarities of 2 or 3. If both of the longitudinal and radial waveforms have a clarity of 2 or 3, flow moves to 1314. At 1314, the method uses the default radial or longitudinal waveform to calculate the MAT. Otherwise, flow moves to 1316.

At 1316, the method determines whether both the longitudinal and radial waveforms have a clarity score of 1. When both of the longitudinal and radial waveforms have a clarity of 1, the method discards the map point and does not calculate a MAT for the map point.

Otherwise, when the decisions at 1308, 1312 and 1314 are all NO, at 1320, the method uses the one of the longitudinal and radial waveforms with the higher clarity score.

Next 1322, the method determines whether all of the map points in the collection have been analyzed. If so, flow stops. Otherwise, flow moves to 1324 where the next map point is selected from the collection. The process is then repeated for the next map point from 1304 to 1322.

FIG. 14 illustrates examples of motion waveforms that may be analyzed by the process of FIG. 13 for radial and longitudinal motion components. In the example of FIG. 14, the radial direction component is the default. In FIG. 14, example A, the radial component is assigned a clarity of 2 for onset and a clarity of 2 for end systole, while the longitudinal component is assigned a clarity of 3 for onset and a clarity of 3 for end systole. Thus, when the method seeks to assign the MAT based on onset or end systole, the method would utilize the longitudinal motion waveform component.

In FIG. 14, example B, the radial component is assigned a clarity of 3 for onset and a clarity of 1 for end systole, while the longitudinal component is assigned a clarity of 3 for onset and a clarity of 3 for end systole. Thus, when the method seeks to assign the MAT based on onset, the method would utilize the radial motion waveform component. When the method seeks to assign the MAT based on end systole, the method would utilize the longitudinal motion waveform component.

In FIG. 14, example C, the radial component is assigned a clarity of 3 for onset and a clarity of 3 for end systole, while the longitudinal component is assigned a clarity of 3 for onset and a clarity of 3 for end systole. Thus, when the method seeks to assign the MAT based on onset, the method would utilize the radial motion waveform component. When the method seeks to assign the MAT based on end systole, the method would utilize the radial motion waveform component.

In FIG. 14, example D, the radial component is assigned a clarity of 3 for onset and a clarity of 1 for end systole, while the longitudinal component is assigned a clarity of 2 for onset and a clarity of 3 for end systole. Thus, when the method seeks to assign the MAT based on onset, the method would utilize the radial motion waveform component. When the method seeks to assign the MAT based on end systole, the method would utilize the longitudinal motion waveform component.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

The invention claimed is:

1. A method for determining mechanical activation times (MATs) associated with map points of a heart, the method comprising:
utilizing one or more processors to perform the following operations:
obtaining a region of interest (ROI) data set comprising a plurality of point specific (PS) motion data representative of wall motion at select map points,
selecting a current map point from the select map points and a corresponding collection of PS motion data for the current map point, the collection of PS motion data comprising a set of directional motion components indicative of wall motion along at least first and second directions at the current map point;
analyzing a component preference characteristic (CPC) of the set of directional motion components for the current map point, wherein the CPC is at least one of i) a time characteristic that is to be identified from the collection of PS motion data, ii) a location characteristic indicating a wall segment in which the current map point is located, and/or iii) a quality characteristic indicating a clarity of a characteristic of interest in motion waveforms;
identifying the wall motion as predominately along the first or second directions based on the CPC of the set of directional motion components for the current map point;
designating, by a mapping tool, a first directional motion component from the set of directional motion components based on identifying that wall motion is predominately along the first direction, wherein the designating comprises selecting between the first directional motion component and a second directional motion component; and
determining a MAT for the current map point of the heart based on the first designated directional motion component.

2. The method of claim 1, wherein the CPC represents the time characteristic that is to be identified from the collection of PS motion data, the method selecting between the first and second directional motion component based on the time characteristic representing one of an onset and an end for one of a contraction action and an extension action of a region of interest.

3. The method of claim 2, wherein the determining operation determines the MAT based on an earlier occurrence of a contraction onset exhibited in one of radial or longitudinal component motion waveforms that correspond to the first and second directional motion component, respectively.

4. The method of claim 2, wherein the determining operation determines the MAT based on a later occurrence of a contraction end event exhibited in one of radial or longitudinal component motion waveforms that correspond to the first and second directional motion component, respectively.

5. The method of claim 1, wherein the set of directional motion components includes radial, circumferential and longitudinal component motion waveforms, the designating operation selecting at least two of the radial, circumferential and longitudinal component motion waveforms as the first directional motion component and a third directional motion component to be used during the determining operation to determine the MAT.

6. The method of claim 1, wherein the CPC represents the location characteristic indicating the wall segment in which the current map point is located, the analyzing comprising identifying the wall motion as predominately along the first or second directions based on the location characteristic representing an apical, middle, basal, anteroseptal, anterior, lateral, septal, inferior, or posterior wall segment, the first directional motion component designated to be associated with the wall segment in which the current map point is located as indicated by the CPC.

7. The method of claim 1, wherein the analyzing operation includes identifying the current map point in a wall segment for which wall motion is predominately in a radial direction or predominately in a longitudinal direction;
wherein the designating operation selects a longitudinal component motion waveform and the determining operation uses the longitudinal component motion waveform associated with the current map point to identify the MAT, when the wall motion is predominately in the longitudinal direction,
wherein the designating operation selects a longitudinal component motion waveform and the determining operation uses the radial component motion waveform associated with the current map point to identify the MAT, when the wall motion is predominately in the radial direction.

8. The method of claim 1, wherein the CPC represents the quality characteristic indicating the clarity of the characteristic of interest in motion waveforms associated with the set of directional motion components.

9. The method of claim 1, wherein the analyzing operation comprises analyzing one or more characteristics of interest of motion waveforms for the set of directional motion components to identify the wall motion as predominately along the first or second directions, the characteristics of interest including at least one of angle of a select waveform segment, a presence of notches in a vicinity of onset and/or end systole, a number of peaks/valleys, or a number of changes in slope in the motion waveforms.

10. The method of claim 1, further comprising assigning a clarity score to each of the set of directional motion components, the CPC based on the clarity scores, the clarity scores indicating a distinctiveness of a characteristic of interest in the set of directional motion components, the analyzing operation utilizing the clarity scores to identify the wall motion as predominately along the first or second directions.

11. The method of claim 1, further comprising generating motion component waveforms for at least a portion of the select map points based on the collection of PS motion data, the motion component waveforms indicative of wall motion at the corresponding select map points along the at least corresponding first and second directions.

12. The method of claim 11, wherein the analyzing comprises analyzing a CPC of the motion component waveforms associated with the current map point, and designating a first motion component waveform from the motion component waveforms based on the analysis of the CPC.

13. A system for determining mechanical activation times (MATs) associated with map points of a heart, the system comprising an intravascular mapping tool comprising:
　　a data storage configured to store a region of interest (ROI) data set comprising a plurality of point specific (PS) motion data representative of motion at select map points proximate to the heart, a collection of the PS motion data comprising a set of directional motion components indicative of motion along at least corresponding first and second directions at a current map point from the select map points; and
　　a processor configured to:
　　　　select the current map point from the select map points;
　　　　analyze a component preference characteristic (CPC) of the set of directional motion components for the current map point, wherein the CPC is at least one of i) a time characteristic that is to be identified from the collection of PS motion data, ii) a location characteristic indicating a wall segment in which the current map point is located, and/or iii) a quality characteristic indicating a clarity of a characteristic of interest in motion waveforms;
　　　　identify the wall motion as predominately along the first or second directions based on the CPC of the set of directional motion components for the current map point;
　　　　designate a first directional motion component from the set of directional motion components based on identifying that wall motion is predominately along the first direction, wherein the designate operation comprises selecting between the first directional motion component and a second directional motion component; and
　　　　determine a MAT for the current map point of the heart based on the first designated directional motion component.

14. The system of claim 13, wherein the CPC represents the time characteristic that is to be identified from the collection of PS motion data, and wherein the processor is configured to select between the first and second directional motion components based on the time characteristic representing one of an onset and an end for one of a contraction action and an extension action of a region of interest.

15. The system of claim 14, wherein the processor is configured to determine the MAT based on an earlier occurrence of a contraction onset exhibited in one of radial or longitudinal component motion waveforms that correspond to the first and second directional motion component, respectively.

16. The system of claim 14, wherein the processor is configured to determine the MAT based on a later occurrence of a contraction end event exhibited in one of radial or longitudinal component motion waveforms that correspond to the first and second directional motion component, respectively.

17. The system of claim 13, wherein the set of directional motion components include radial, circumferential and longitudinal component motion waveforms, the processor configured to select at least two of the radial, circumferential and longitudinal component motion waveforms as the first directional motion component and a third directional motion component to be used during the determining operation to determine the MAT.

18. The system of claim 13, wherein the CPC represents the location characteristic indicating the wall segment in which the current map point is located, the processor configured to identify the wall motion as predominately along the first or second directions based on the location characteristic representing an apical, middle, basal, anteroseptal, anterior, lateral, septal, inferior, or posterior wall segment, and wherein the processor is further configured to designate the first directional motion component associated with the wall segment in which the current map point is located as indicated by the CPC.

19. The system of claim 13, wherein the processor is configured to:
　　identify the current map point as in a wall segment for which wall motion is predominately in a radial direction or predominately in a longitudinal direction;
　　select a longitudinal component motion waveform associated with the current map point to identify the MAT, when the wall motion is predominately in the longitudinal direction, and
　　select a radial component motion waveform associated with the current map point to identify the MAT, when the wall motion is predominately in the radial direction.

20. The system of claim 13, wherein the CPC represents the quality characteristic indicating the clarity of the characteristic of interest in motion waveforms associated with the set of directional motion components.

21. The system of claim 13, wherein the processor is configured to analyze one or more characteristics of interest of motion waveforms for the set of directional motion components to identify the wall motion as predominately along the first or second directions, the characteristics of interest including at least one of angle of a select waveform segment, a presence of notches in a vicinity of onset and/or end systole, a number of peaks/valleys, or a number of changes in slope in motion waveforms.

22. The system of claim 13, wherein the processor is configured to assign a clarity score to each of the set of directional motion components, the CPC based on the clarity scores, the clarity scores indicating a distinctiveness of a characteristic of interest in the set of directional motion components, the processor configured to utilize the clarity scores to identify the wall motion as predominately along the first or second direction.

23. The system of claim 13, wherein the processor is configured to generate motion component waveforms for at least a portion of the select map points based on the collection of PS motion data, the motion component waveforms indicative of motion at the corresponding select map points along the at least corresponding first and second directions.

24. The system of claim 23, wherein the processor is configured to analyze the CPC of the motion component waveforms associated with the current map point, and designate a first motion component waveform from the motion component waveforms based on the analysis of the CPC.

* * * * *